(12) United States Patent
Corson et al.

(10) Patent No.: US 11,707,445 B2
(45) Date of Patent: Jul. 25, 2023

(54) COMPOSITION FOR BLOCKING ANGIOGENESIS

(71) Applicant: Indiana University Research and Technology Corporation, Indianapolis, IN (US)

(72) Inventors: Timothy William Corson, Fishers, IN (US); Rania Sulaiman, Indianapolis, IN (US)

(73) Assignee: Indiana University Research and Technology Corporation, Indianapolis, IN (US)

( * ) Notice: Subject to any disclaimer, the term of this patent is extended or adjusted under 35 U.S.C. 154(b) by 98 days.

(21) Appl. No.: 17/226,781

(22) Filed: Apr. 9, 2021

(65) Prior Publication Data

US 2021/0228538 A1 Jul. 29, 2021

Related U.S. Application Data

(63) Continuation of application No. 15/780,980, filed as application No. PCT/US2016/062851 on Nov. 18, 2016, now abandoned.

(60) Provisional application No. 62/259,281, filed on Nov. 24, 2015.

(51) Int. Cl.
| | |
|---|---|
| *A61K 31/353* | (2006.01) |
| *A61P 27/02* | (2006.01) |
| *A61K 39/395* | (2006.01) |
| *A61K 31/343* | (2006.01) |
| *A61K 31/335* | (2006.01) |
| *A61K 39/00* | (2006.01) |

(52) U.S. Cl.
CPC .......... *A61K 31/353* (2013.01); *A61K 31/335* (2013.01); *A61K 31/343* (2013.01); *A61K 39/39541* (2013.01); *A61P 27/02* (2018.01); *A61K 2039/505* (2013.01)

(58) Field of Classification Search
None
See application file for complete search history.

(56) References Cited

U.S. PATENT DOCUMENTS

| | | |
|---|---|---|
| 10,238,627 B2 | 3/2019 | Corson et al. |
| 2012/0195858 A1 | 8/2012 | Foernzler et al. |
| 2013/0295094 A1 | 11/2013 | Yancopoulos |
| 2015/0376271 A1 | 12/2015 | Perlroth et al. |

FOREIGN PATENT DOCUMENTS

WO 2014182695 A1 11/2014

OTHER PUBLICATIONS

Sulaiman et al. "A Novel Small Molecule Ameliorates Ocular Neovascularization and Synergizes with anti-VEGF Therapy". Scientific Reports. May 5, 2016; 6:25509. (Year: 2016).*
Basavarajappa et al., Synthesis and Biological Evaluation of Novel Homoisoflavonoids for Retinal Neovascularization; J Med Chem., 2015, vol. 58, No. 12, pp. 5015-5027.
Borisy et al., Systematic discovery of multicomponent therapeutics; PNAS, 2003, vol. 100, No. 13, pp. 7977-7982.
Cai et al., β-Secratase (BACE1) inhibition causes retinal pathology by vascular dysregulation and accumulation of age pigment; EMBO Molecular Medicine, 2012, vol. 4, pp. 980-991.
Hur et al., Homoisoflavanone Inhibits UVB-lnduced Skin Inflammation Through Reduced Cyclooxygenase-2 Expression and NF-KB Nuclear Localization; Journal of Dermatological Science; 2010, vol. 59, pp. 163-169.
Lambert et al., Laser-induced choroidal neovascularization model to study age-related macular degeneration in mice; Nature Protocols, 2013, vol. 8, No. 11, pp. 2197-2211.
Lee et al., First Synthesis of the Antiangigenic Homoisoflavanone, Cremastranone; Org Biomol Chem, 2014, vol. 12, No. 39, pp. 7673-7677.
Poor et al., Reliability of the Mouse Model of Choroidal Neovascularization Induced by Laser Photocoagulation; The Association for Research in Vison and Opthalmology, Inc.; 2014, pp. 6525-6534.
Shao et al., Choroid Sprouting Assay: An Ex Vivo Model of Microvascular Angiogenesis; PLOS one, 12-pages.
Shim et al., Anti-Angiogenic Activity of a Homoisoflavanone from Cremastra appendiculata; Planta Medica; 2004, vol. 70, No. 2, pp. 171-173.
Sulaiman et al., A Simple Optical Coherence Tomography Quantification Method for Choroidal Neovascularization; Journal of Ocular Pharmacology and Therapeutics, 2015, vol. 31, pp. 447-454.
Tanzi, Maria G.; Aflibercept: Bimonthly intiavitreal injection for AMD; Pharmacy Today; 2012, vol. 43, 1-page.

* cited by examiner

*Primary Examiner* — Leslie A. Royds Draper
(74) *Attorney, Agent, or Firm* — Stinson LLP

(57) ABSTRACT

Compositions including the combination of cremastranone analogs and anti-angiogenic agents and the use of the compositions for targeting ocular angiogenesis such as seen in neovascular eye diseases are disclosed.

7 Claims, 15 Drawing Sheets

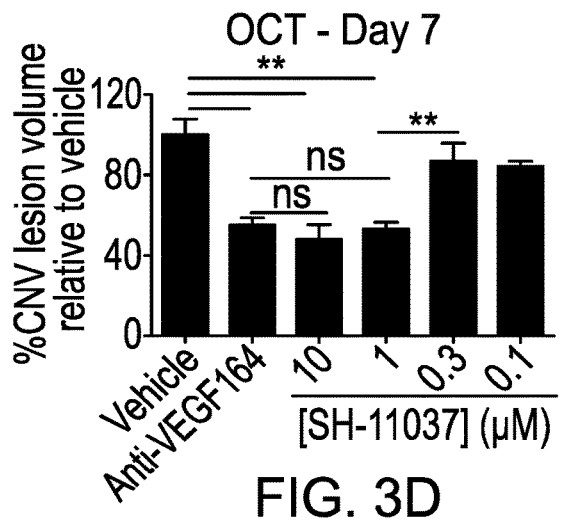
FIG. 3D
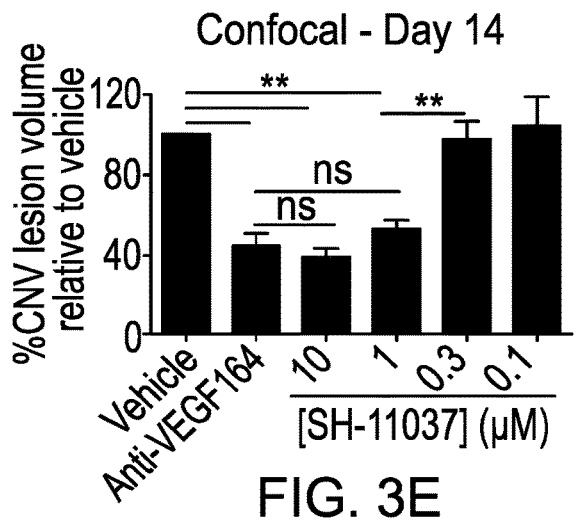
FIG. 3E
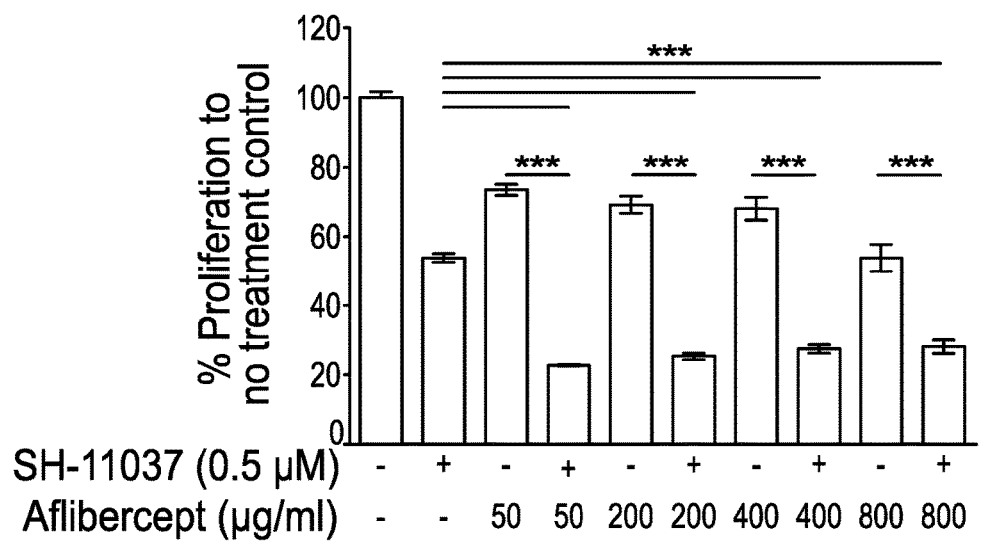
FIG. 4A
FIG. 4B

COMPOSITION FOR BLOCKING ANGIOGENESIS

CROSS-REFERENCE TO RELATED APPLICATIONS

This application is a continuation application of U.S. patent application Ser. No. 15/780,980 filed on Jun. 1, 2018, which claims priority to International Publication Number WO 2017/091473, filed on Nov. 18, 2016, which claims priority to U.S. Provisional Patent Application No. 62/259,281 filed on Nov. 24, 2015, the disclosures of which are hereby expressly incorporated by reference in their entireties.

BACKGROUND OF THE DISCLOSURE

The present disclosure relates generally to compositions for the treatment of angiogenesis-mediated diseases. More particularly, the present disclosure relates to compositions including the combination of cremastranone analogs and anti-angiogenic agents for targeting ocular angiogenesis related to neovascular eye diseases.

Angiogenesis does not occur in the body, except during development and wound repair processes. However, during numerous pathological conditions, angiogenesis occurs, notably in ocular diseases such as retinopathy of prematurity (ROP), diabetic retinopathy (DR), and "wet" age-related macular degeneration (AMD). After pathological angiogenesis occurs, newly formed blood vessels are fragile, porous and not fully differentiated. The formation of such new blood vessels in the eye may lead to hemorrhage, rapid photoreceptor degeneration, and eventual fibrotic scarring, with rapid, permanent vision loss.

Clinical symptoms of DR are seen in 75% of diabetic patients, with 10% of them eventually developing visual impairment. DR is currently the leading cause of blindness among working age adults and accounts for 8% of the legal blindness in the United States. Additionally, almost 2 million Americans are affected by AMD. AMD has an estimated loss of productivity burden of 55.4 billion annually in the United States. Severely affected patients have a very poor quality of life, comparable to that of catastrophic stroke victims or advanced cancer patients in constant pain.

Established treatment modalities for AMD include thermal laser photocoagulation or photodynamic therapy in conjunction with verteporfin. More recently, anti-vascular endothelial growth factor (anti-VEGF) therapies such as pegaptanib, ranibizumab, aflibercept, and bevacizumab have shown success in slowing and even reversing vision loss in some age-related macular degeneration patients. A significant proportion of patients do not respond to these drugs (up to 45% in one series). Further, significant acute, systemic side effects (non-ocular hemorrhage, myocardial infarction, and stroke) indicate that these therapies can act outside the eye even when delivered intravitreally. Blinding intraocular side effects are also possible and the long-term risks of these drugs are still unclear. Moreover, because they are biologics, the cost-benefit ratios of these drugs are unfavorable. For instance, ranibizumab costs approximately $2,000 per monthly dose, rendering these treatments unaffordable for many patients. Since recurrence after treatment cessation can also occur, treatment with drug combinations targeting different pathways that truly eradicate the disease has been touted as the future of therapy for this disease.

A similar situation exists for retinopathy of prematurity (ROP). Retinopathy of prematurity (ROP) is characterized by abnormal blood vessel growth in the neonatal retina. The disease develops in two stages. In the first, hyperoxic stage, from 22 to 30 weeks' gestational age, high oxygen levels (as experienced in the ventilated, extrauterine environment compared to in utero) lead to decreased VEGF production and subsequent cessation of vascularization. In the second phase, photoreceptors mature and the avascular retina grows and becomes hypoxic, prompting production of VEGF. VEGF is essential for signaling normal vessel growth during development, but when aberrantly expressed at high levels, causes improper neovessel growth. Neovessels, extending into the vitreous, do not oxygenate the retina well and easily rupture, leading to retinal ganglion cell and photoreceptor loss, retinal detachment, and blindness.

In 2010, 12% of children in the United States were born prematurely, and 1.5% were very low birth weight (VLBW; <1500 g). Almost 70% of these VLBW infants were likely to develop ROP, which is caused by aberrant angiogenesis after exposure to postnatal hyperoxia. The disease is estimated to cause visual loss in 1300 children per year in the United States, and severe visual impairment in a further 500 children per year. Overall, between 6% and 18% of childhood blindness is attributable to ROP. Moreover, as more and more children survive premature birth in middle income countries due to improvements in neonatal intensive care, ROP is becoming more prevalent worldwide. Aside from the acute risk of blindness, in childhood and even as adults, ROP survivors are more likely than the general population to develop posterior segment pathology, retinal detachment, myopia, amblyopia, strabismus, early cataract, and glaucoma.

Although biologic treatments are effective for ROP and show fewer side effects than surgical treatments, there remain significant concerns about lasting toxic or developmental effects in neonates, especially since these drugs can have systemic actions even when delivered locally. Accordingly, there is a critical unmet need for novel small molecules to treat ocular neovascularization disorders as well as other angiogenesis-mediated diseases, to complement the existing approaches and allow lower-dose, combination therapies.

The bulb of the Orchidaceae family member *Cremastra appendiculata* (D. Don) is a traditional medicine in East Asia, used internally to treat several cancers, and externally for skin lesions. Several natural products have been extracted from this plant, but perhaps most intriguing of these is a compound known as cremastranone, previously known by the generic name "homoisoflavanone" (FIG. 1A). Cremastranone (1), 5,7-dihydroxy-3-(3-hydroxy-4-methoxybenzyl)-6-methoxychroman-4-one, is a member of a small group of known homoisoflavanones and has also been isolated from members of the Hyacinthaceae.

The natural cremastranone has been found to be an effective inhibitor of angiogenesis in vivo. In the chick chorioallantoic membrane model, cremastranone was as effective as retinoic acid in blocking new vessel growth induced by bFGF. Cremastranone also showed efficacy in blocking pathogenic neovascularization in an oxygen-induced retinopathy model of retinopathy of prematurity and in the laser photocoagulation murine model of choroidal neovascularization. These models are widely used for treatment evaluations in these ocular neovascular disorders. Additionally, injection of 10 µM cremastranone into the vitreous of normal adult mice showed no cytotoxic or inflammatory effects on the retina, nor did it induce apoptosis of retinal cells.

Further, as previously reported in WO2014/182695, synthetic cremastranone analogs have been made that were found to be more potent than the parent compound, cremastranone, with about 10-fold antiproliferative selectivity towards human retinal endothelial cells (HRECs) over macrovascular endothelial cells, and negligible effects on other ocular cell types. In particular, analog SH-11037 (2) (FIG. 1B) inhibited HREC proliferation, migration, and tube formation in a concentration-dependent manner, without inducing apoptosis. Together, these data provided a strong in vitro indication of SH-11037's antiangiogenic activity without cytotoxicity. Moreover, it was shown that SH-11037 significantly suppressed retinal neovascularization in the oxygen-induced retinopathy (OIR) model of retinopathy of prematurity (ROP), a blinding disease in children associated with aberrant angiogenesis.

Based on the foregoing, it would be highly advantageous to combine the antiangiogenic therapeutic potential of synthetic cremastranone analogues (e.g., SH-11037) with other ocular neovascularization therapies. Further, as surprisingly found, SH-11037 had a strong antiangiogenic potential on choroidal neovascularization (CNV) in the absence of ocular toxic effects and could synergize with existing anti-VEGF drugs as compared to the analogs and existing anti-VEGF drugs alone.

BRIEF DESCRIPTION OF THE DISCLOSURE

The present disclosure is generally related to compositions including the combination of cremastranone analogs and anti-angiogenic agents for targeting ocular angiogenesis related to neovascular eye diseases. The compositions are shown herein to have synergistic antiangiogenic effects.

In one aspect, the present disclosure is directed to a composition comprising a synthetic compound comprising formula (I)

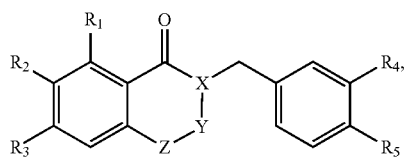

wherein $R_1$, $R_2$, $R_3$, $R_4$, and $R_5$ are independently selected from the group consisting of hydrogen, hydroxyl, alkoxy, substituted alkoxy, alkyl carbonyloxy, substituted alkyl carbonyloxy, alkyl carbonyl, substituted alkyl carbonyl, aryl carbonyloxy, substituted aryl carbonyloxy, halogen, amino, nitro, hydrocarbyl and substituted hydrocarbyl; and X, Y, and Z are independently selected from the group consisting of carbon, nitrogen, and oxygen; and an anti-angiogenic agent. In one particular embodiment, the synthetic compound is SH-11037.

In another aspect, the present disclosure is directed to a composition comprising a synthetic compound comprising formula (II)

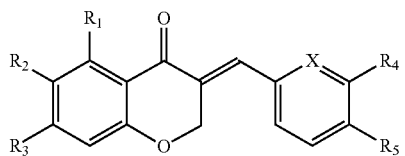

wherein $R_1$, $R_2$, $R_3$, $R_4$, and $R_5$ are independently selected from the group consisting of hydrogen, hydroxyl, alkoxy, substituted alkoxy, alkyl carbonyloxy, substituted alkyl carbonyloxy, alkyl carbonyl, substituted alkyl carbonyl, aryl carbonyloxy, substituted aryl carbonyloxy, halogen, amino, nitro, hydrocarbyl and substituted hydrocarbyl; and X is selected from the group consisting of carbon and nitrogen; and an anti-angiogenic agent.

In yet another aspect, the present disclosure is directed to a composition comprising a synthetic compound comprising formula (III)

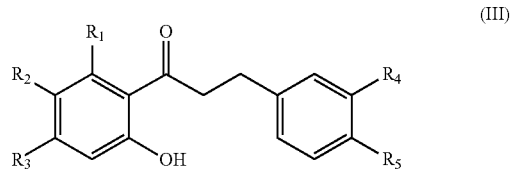

wherein $R_1$, $R_2$, $R_3$, $R_4$, and $R_5$ are independently selected from the group consisting of hydrogen, hydroxyl, alkoxy, substituted alkoxy, alkyl carbonyloxy, substituted alkyl carbonyloxy, alkyl carbonyl, substituted alkyl carbonyl, aryl carbonyloxy, substituted aryl carbonyloxy, halogen, amino, nitro, hydrocarbyl and substituted hydrocarbyl; and an anti-angiogenic agent.

In another aspect, the present disclosure is directed to a composition comprising a synthetic compound comprising formula (IV)

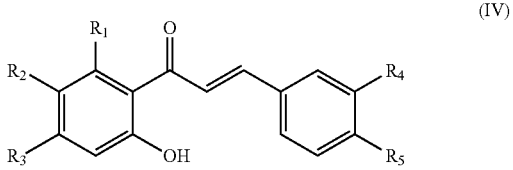

wherein $R_1$, $R_2$, $R_3$, $R_4$, and $R_5$ are independently selected from the group consisting of hydrogen, hydroxyl, alkoxy, substituted alkoxy, alkyl carbonyloxy, substituted alkyl carbonyloxy, alkyl carbonyl, substituted alkyl carbonyl, aryl carbonyloxy, substituted aryl carbonyloxy, halogen, amino, nitro, hydrocarbyl and substituted hydrocarbyl; and an anti-angiogenic agent.

In another aspect, the present disclosure is directed to a composition comprising a synthetic compound comprising formula (V)

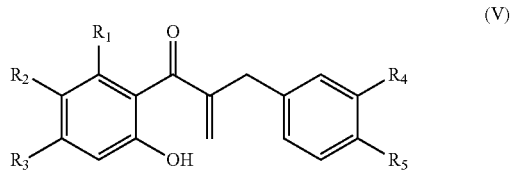

wherein $R_1$, $R_2$, $R_3$, $R_4$, and $R_5$ are independently selected from the group consisting of hydrogen, hydroxyl, alkoxy, substituted alkoxy, alkyl carbonyloxy, substituted alkyl carbonyloxy, alkyl carbonyl, substituted alkyl carbonyl, aryl carbonyloxy, substituted aryl carbonyloxy, halogen, amino, nitro, hydrocarbyl and substituted hydrocarbyl; and an anti-angiogenic agent.

In another aspect, the present disclosure is directed to a composition comprising a synthetic compound comprising formula (VI)

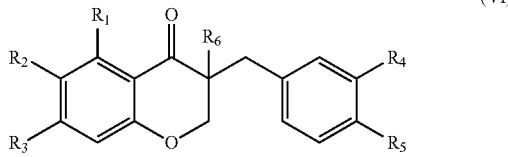

(VI)

wherein $R_1$, $R_2$, $R_3$, $R_4$, and $R_5$ are independently selected from the group consisting of hydrogen, hydroxyl, alkoxy, substituted alkoxy, alkyl carbonyloxy, substituted alkyl carbonyloxy, alkyl carbonyl, substituted alkyl carbonyl, aryl carbonyloxy, substituted aryl carbonyloxy, halogen, amino, nitro, hydrocarbyl and substituted hydrocarbyl; and $R_6$ is selected from the group consisting of hydrogen and substituted hydrocarbyl; and an anti-angiogenic agent.

In another aspect, the present disclosure is directed to a composition comprising a synthetic compound comprising formula (VII)

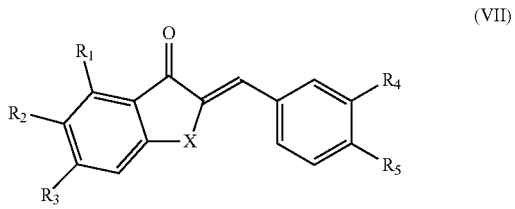

(VII)

wherein $R_1$, $R_2$, $R_3$, $R_4$, and $R_5$ are independently selected from the group consisting of hydrogen, hydroxyl, alkoxy, substituted alkoxy, alkyl carbonyloxy, substituted alkyl carbonyloxy, alkyl carbonyl, substituted alkyl carbonyl, aryl carbonyloxy, substituted aryl carbonyloxy, halogen, amino, nitro, hydrocarbyl and substituted hydrocarbyl; and X is selected from the group consisting of carbon, nitrogen, and oxygen; and an anti-angiogenic agent.

In another aspect, the present disclosure is directed to a composition comprising a synthetic compound comprising formula (VIII)

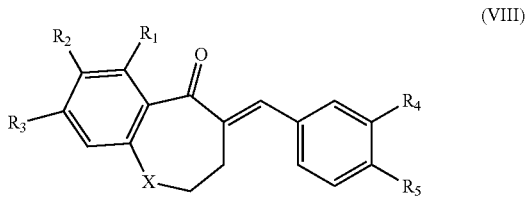

(VIII)

wherein $R_1$, $R_2$, $R_3$, $R_4$, and $R_5$ are independently selected from the group consisting of hydrogen, hydroxyl, alkoxy, substituted alkoxy, alkyl carbonyloxy, substituted alkyl carbonyloxy, alkyl carbonyl, substituted alkyl carbonyl, aryl carbonyloxy, substituted aryl carbonyloxy, halogen, amino, nitro, hydrocarbyl and substituted hydrocarbyl; and X is selected from the group consisting of carbon, nitrogen, and oxygen; and an anti-angiogenic agent.

In yet another aspect, the present disclosure is directed to methods of treating a neovascular eye disease in a subject in need thereof using the compositions described above. The methods comprise administering an effective amount of the compositions and a pharmaceutically acceptable carrier.

In another aspect, the present disclosure is directed to methods of treating an angiogenesis-mediated disease in a subject in need thereof using the compositions described above. The methods comprise administering an effective amount of the compositions and a pharmaceutically acceptable carrier.

BRIEF DESCRIPTION OF THE DRAWINGS

The disclosure will be better understood, and features, aspects and advantages other than those set forth above will become apparent when consideration is given to the following detailed description thereof. Such detailed description makes reference to the following drawings, wherein:

(FIG. 1B) SH-11037 (2).

FIG. 2A includes representative images of H&E stained retinas, scale bars=100 μm, and quantification of the indicated A/B ratio show the absence of short- or long-term changes in retinal layers at any given concentration of SH-11037. P>0.05, Student's t-tests, Mean±SEM, n=8 eyes/treatment. FIG. 2B depicts immunofluorescence staining revealing no differences between SH-11037 treatment and vehicle control in GFAP, cleaved caspase 3, TUNEL, and MCP1 (labeled with an "X") as markers of retinal injury, apoptosis, or inflammation, respectively. Laser injured eyes were stained for the same markers as a positive control; white arrows indicate the increased expression of respective markers. Nuclei are stained with DAPI. Scale bars=20 μm. GCL, ganglion cell layer; ONL, outer nuclear layer; RPE, retinal pigment epithelium.

FIGS. 3A-3E depict the effect of SH-11037 on CNV lesion volume. FIG. 3A includes representative optical coherence tomography (OCT) images obtained 7 days post-laser, showing CNV lesions of vehicle (left), anti-VEGF164 (middle), and 1 μM SH-11037 (right). Scale bars=100 μm. FIG. 3B includes representative images from fluorescein angiography (FA) 14 days post-laser.

FIG. 3C includes representative images from confocal microscopy for agglutinin-stained CNV lesions 14 days postlaser, scale bars=50 μm. FIG. 3D shows the quantification of CNV lesion volumes from OCT images at day 7 using ellipsoid volume measurement. FIG. 3E shows the quantification of CNV lesion volumes from Z-stack images at day 14 using ImageJ software. **P<0.01, one-way ANOVA, Tukey's post hoc tests, ns; non significant. Mean±SEM, n=12 eyes/treatment.

FIGS. 4A-4G depict the ability of SH-11037 to synergize with anti-VEGF therapy in vitro and in vivo. FIG. 4A depicts the effect of 0.5 μM SH-11037, different concentrations of aflibercept (Eylea, Regeneron) and SH-11037/aflibercept combinations on HREC proliferation was tested using AlamarBlue fluorescence assay, **P<0.001 as indicated, one-way ANOVA with Tukey's post hoc tests. Mean±SEM, n=3. Representative data from duplicate experiments. FIG. 4B depicts calculations of the excess percentage inhibition over highest single agent (HSA) activity and excess over Bliss additivity. Values<0 are in white boxes, values from 1-10 are in boxes with dots, and values>10, indicating synergy, are in boxes with hatching. FIG. 4C includes representative images from confocal microscopy of agglutinin stained CNV lesions for combination treatment; 1 ng mouse Anti- VEGF164 antibody (comparable to bevacizumab)/1 μM SH-11037 (Combo (1/1)) compared to individual SH-11037 and anti-VEGF treatments and vehicle control, scale bars=50 μm. FIG. 4D depicts dose-dependent inhibition of the volume of CNV lesions by anti-VEGF injections. No difference was observed between anti-VEGF164+vehicle compared to anti-VEGF164 alone. FIG. 4E depicts the quantification of the CNV lesion volume showing a substitution of anti-VEGF by SH-11037. The combination of 1 ng/1 μM produces a similar effect to that observed by the 5 ng dose of anti-VEGF alone. The combination of 0.2 ng/0.3 μM is significantly different from individual treatments alone, and exceeds Bliss additivity and HSA by 36% and 37%, respectively, indicating synergy. The graphs in FIGS. 4D and 4E** are quantification of CNV lesion volumes from Z-stack images. *P<0.05, P<0.01, P<0.0001, one-way ANOVA, Tukey's post hoc tests. Mean±SEM, n=12 eyes/treatment. FIG. 4F depicts representative mean ERG responses of the combination (0.2/0.3) and vehicle treatments. FIG. 4G** depicts quantification of scotopic a- and b-waves and photopic b-wave, showing no difference in retinal function (stimulus: scotopic=2.5, photopic=25 cd·s/m2). P>0.05, Student's t-test. Mean±s.e.m., n=6 eyes/treatment.

FIG. 5A shows that isolectin-stained retinal vasculature does not differ between 100 μM SH-11037 and vehicle treated control eyes 14 days post-injection. Scale bar=50 μm. FIG. 5B shows the quantification of retinal vasculature as vessels area per unit area of retina analyzed. No difference was seen between SH-11037 and vehicle control. FIG. 5C depict representative mean ERG responses. FIG. 5D show the quantification of scotopic a- and b-waves and photopic b wave, showing no difference in retinal function (stimulus: scotopic=2.5, photopic=25 cd/s/m$^2$). P>0.05, Student's t-test. Mean±SEM, n=6 mice/treatment.

FIG. 6A includes representative images of choroidal sprouts formed 48 hours after treatment with indicated SH-11037 concentrations or DMSO control, scale bars=1000 μm. FIG. 6B shows the quantification of sprouting distance from the edge of the choroid tissue piece to the end of the sprouts averaged from four perpendicular directions using ImageJ software. **P<0.001, two-way ANOVA, Dunnett's post hoc test, Mean±SEM. n=4 from two independent experiments. FIG. 6C** shows representative images of trypan blue stained choroidal sprouts 48 hours after treatment with DMSO and 1 μM SH-11037 to assess cell viability, scale bars=1000 μm.

FIG. 7A includes representative images from confocal microscopy for agglutinin-stained CNV lesions for 5 ng anti-VEGF164 and 10 μM SH-11037 compared to vehicle treatment and 5 days control, scale bars=50 μm. FIG. 7B shows the quantification of CNV lesion vascular volumes from Z-stack images at day 14 using ImageJ software. *P<0.05, ***P<0.001, one-way ANOVA, Tukey's post hoc tests. Mean±SEM, n=12 eyes/treatment.

DETAILED DESCRIPTION

Unless defined otherwise, all technical and scientific terms used herein have the same meaning as commonly understood by one of ordinary skill in the art to which the disclosure belongs. Although any methods and materials similar to or equivalent to those described herein can be used in the practice or testing of the present disclosure, the preferred methods and materials are described below.

The present disclosure is directed to compositions including the combination of cremastranone analogs and antiangiogenic agents for targeting ocular angiogenesis related to neovascular eye diseases. Typically, the synthetic cremastranone analog for use in the composition comprises formula (I)

Figure 1A:
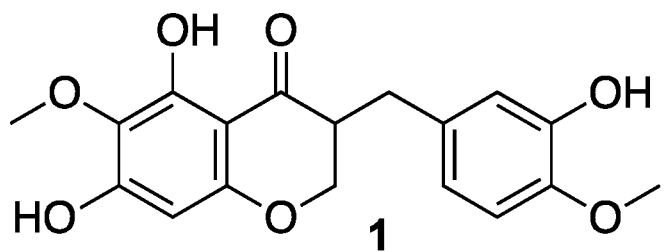
FIGS. 1A & 1B depict the structures of (FIG. 1A) natural cremastranone (1)
Figure 1B:
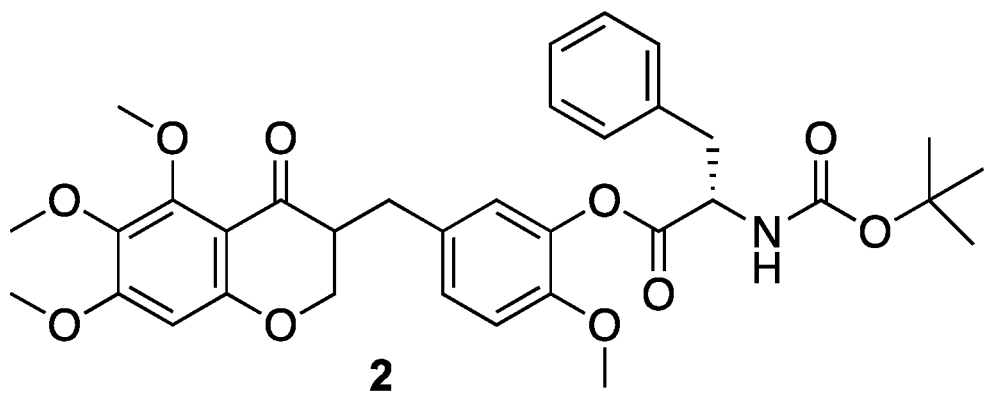

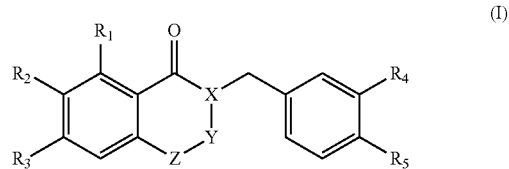

wherein $R_1$, $R_2$, $R_3$, $R_4$, and $R_5$ are independently selected from the group consisting of hydrogen, hydroxyl, alkoxy, substituted alkoxy, alkyl carbonyloxy, substituted alkyl carbonyloxy, alkyl carbonyl, substituted alkyl carbonyl, aryl carbonyloxy, substituted aryl carbonyloxy, halogen, amino, nitro, hydrocarbyl and substituted hydrocarbyl; and X, Y, and Z are independently selected from the group consisting of carbon, nitrogen, and oxygen. In one particular aspect, the present disclosure includes the cremastranone analog SH-11037, shown in FIG. 1B.

In another aspect, the synthetic cremastranone analog comprises formula (II)

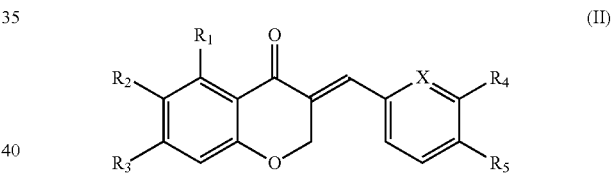

wherein $R_1$, $R_2$, $R_3$, $R_4$, and $R_5$ are independently selected from the group consisting of hydrogen, hydroxyl, alkoxy, substituted alkoxy, alkyl carbonyloxy, substituted alkyl carbonyloxy, alkyl carbonyl, substituted alkyl carbonyl, aryl carbonyloxy, substituted aryl carbonyloxy, halogen, amino, nitro, hydrocarbyl and substituted hydrocarbyl; and X is selected from the group consisting of carbon and nitrogen.

In another aspect, the synthetic cremastranone analog comprises formula (III)

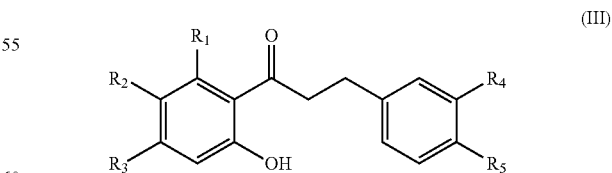

wherein $R_1$, $R_2$, $R_3$, $R_4$, and $R_5$ are independently selected from the group consisting of hydrogen, hydroxyl, alkoxy, substituted alkoxy, alkyl carbonyloxy, substituted alkyl carbonyloxy, alkyl carbonyl, substituted alkyl carbonyl, aryl carbonyloxy, substituted aryl carbonyloxy, halogen, amino, nitro, hydrocarbyl and substituted hydrocarbyl.

In another aspect, the synthetic cremastranone analog comprises formula (IV)

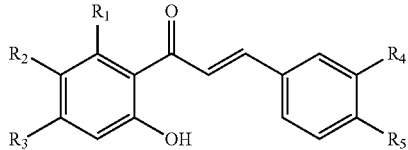
(IV)

wherein $R_1$, $R_2$, $R_3$, $R_4$, and $R_5$ are independently selected from the group consisting of hydrogen, hydroxyl, alkoxy, substituted alkoxy, alkyl carbonyloxy, substituted alkyl carbonyloxy, alkyl carbonyl, substituted alkyl carbonyl, aryl carbonyloxy, substituted aryl carbonyloxy, halogen, amino, nitro, hydrocarbyl and substituted hydrocarbyl.

In another aspect, the synthetic cremastranone analog comprises formula (V)

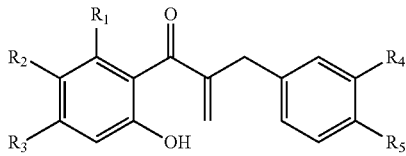
(V)

wherein $R_1$, $R_2$, $R_3$, $R_4$, and $R_5$ are independently selected from the group consisting of hydrogen, hydroxyl, alkoxy, substituted alkoxy, alkyl carbonyloxy, substituted alkyl carbonyloxy, alkyl carbonyl, substituted alkyl carbonyl, aryl carbonyloxy, substituted aryl carbonyloxy, halogen, amino, nitro, hydrocarbyl and substituted hydrocarbyl.

In another aspect, the synthetic cremastranone analog comprises formula (VI)

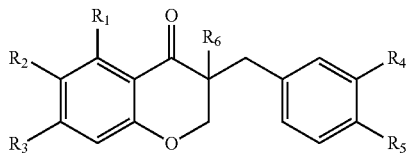
(VI)

wherein $R_1$, $R_2$, $R_3$, $R_4$, and $R_5$ are independently selected from the group consisting of hydrogen, hydroxyl, alkoxy, substituted alkoxy, alkyl carbonyloxy, substituted alkyl carbonyloxy, alkyl carbonyl, substituted alkyl carbonyl, aryl carbonyloxy, substituted aryl carbonyloxy, halogen, amino, nitro, hydrocarbyl and substituted hydrocarbyl; and $R_6$ is selected from the group consisting of hydrogen and substituted hydrocarbyl.

In another aspect, the synthetic cremastranone analog comprises formula (VII)

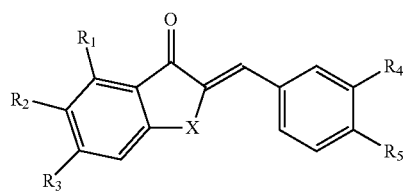
(VII)

wherein $R_1$, $R_2$, $R_3$, $R_4$, and $R_5$ are independently selected from the group consisting of hydrogen, hydroxyl, alkoxy, substituted alkoxy, alkyl carbonyloxy, substituted alkyl carbonyloxy, alkyl carbonyl, substituted alkyl carbonyl, aryl carbonyloxy, substituted aryl carbonyloxy, halogen, amino, nitro, hydrocarbyl and substituted hydrocarbyl; and X is selected from the group consisting of carbon, nitrogen, and oxygen.

In another aspect, the synthetic cremastranone analog comprises formula (VIII)

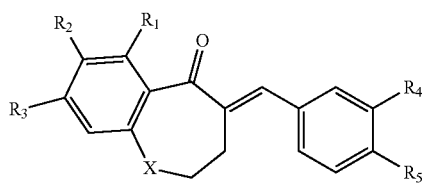
(VIII)

wherein $R_1$, $R_2$, $R_3$, $R_4$, and $R_5$ are independently selected from the group consisting of hydrogen, hydroxyl, alkoxy, substituted alkoxy, alkyl carbonyloxy, substituted alkyl carbonyloxy, alkyl carbonyl, substituted alkyl carbonyl, aryl carbonyloxy, substituted aryl carbonyloxy, halogen, amino, nitro, hydrocarbyl and substituted hydrocarbyl; and X is selected from the group consisting of carbon, nitrogen, and oxygen.

Exemplary synthetic compounds for use in the compositions of the present disclosure include the synthetic cremastranone analogues as disclosed and discussed in WO2014/182695. For example, suitable synthetic cremastranone analogues include those shown in Table 1.

TABLE 1

Synthetic Cremastranone Analogues

| Compound No. | Structure |
|---|---|
| SH-11052 (2) | (structure shown) |

TABLE 1-continued

Synthetic Cremastranone Analogues

| Compound No. | Structure |
|---|---|
| 3a | 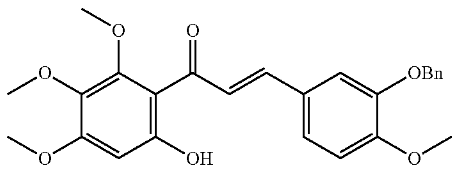 |
| 3b | 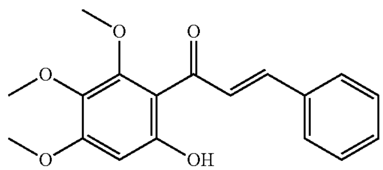 [SMILES: COc1cc(O)c(C(=O)/C=C/c2ccccc2)c(OC)c1OC] |
| 4a | 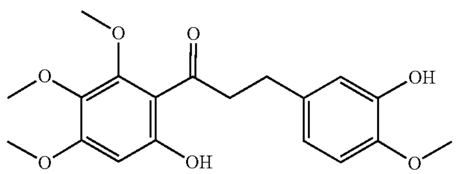 |
| 4b | 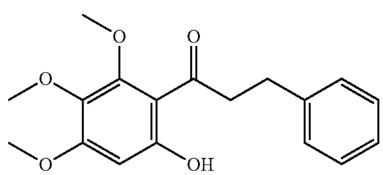 [SMILES: COc1cc(O)c(C(=O)CCc2ccccc2)c(OC)c1OC] |
| 4c | 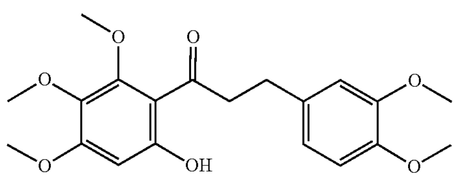 |
| 5 | 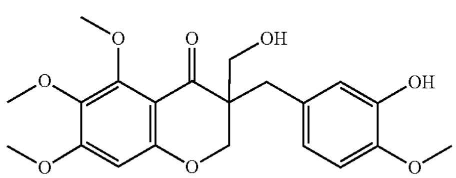 |
| 6a | 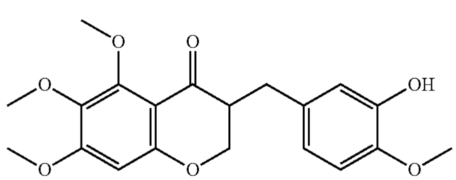 |
| 6b | 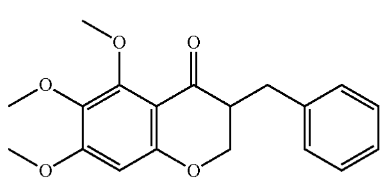 [SMILES: COc1cc2c(c(OC)c1OC)C(=O)C(Cc1ccccc1)CO2] |

TABLE 1-continued

Synthetic Cremastranone Analogues

| Compound No. | Structure |
|---|---|
| SH-11037 (6c) | 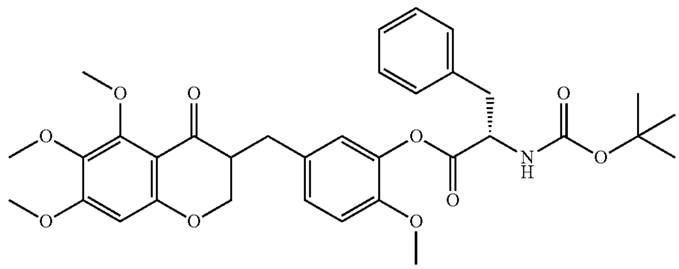 [SMILES: COc1ccc(CC2COc3cc(OC)c(OC)c(OC)c3C2=O)cc1OC(=O)[C@H](Cc1ccccc1)NC(=O)OC(C)(C)C] |
| 6d | 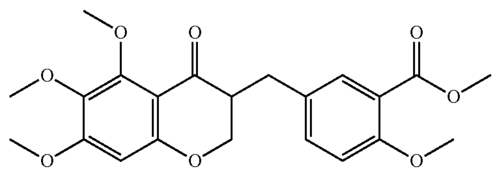 |
| 6e | 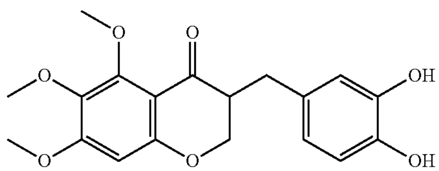 [SMILES: COc1cc2c(c(OC)c1OC)C(=O)C(Cc1ccc(O)c(O)c1)CO2] |
| 6f | 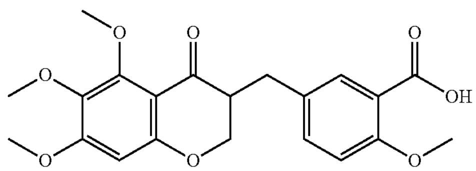 |
| 7 | 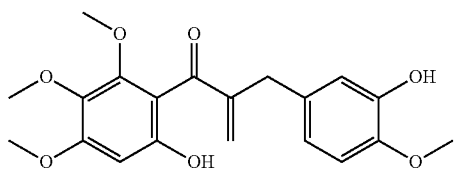 |
| 8a | 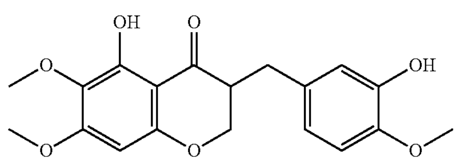 |
| 8b | 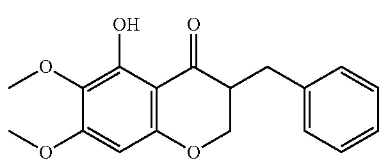 [SMILES: COc1cc2c(c(O)c1OC)C(=O)C(Cc1ccccc1)CO2] |
| 8c | 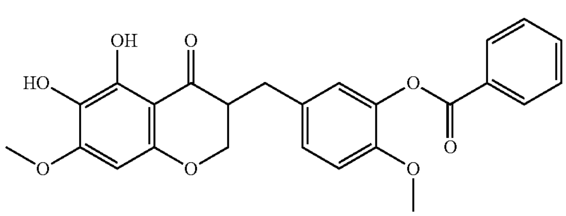 [SMILES: COc1ccc(CC2COc3cc(OC)c(O)c(O)c3C2=O)cc1OC(=O)c1ccccc1] |

TABLE 1-continued

Synthetic Cremastranone Analogues

| Compound No. | Structure |
| --- | --- |
| 8d | 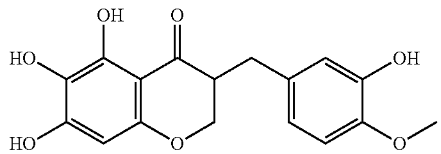 [SMILES: COc1ccc(CC2COc3cc(O)c(O)c(O)c3C2=O)cc1O] |
| 9a | 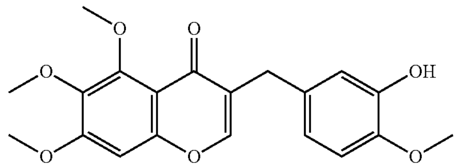 |
| 9b | 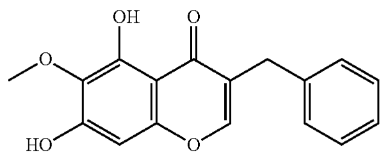 [SMILES: COc1c(O)cc2occ(Cc3ccccc3)c(=O)c2c1O] |
| 10a | 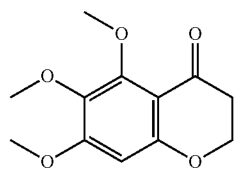 [SMILES: COc1cc2c(c(OC)c1OC)C(=O)CCO2] |
| 10b | 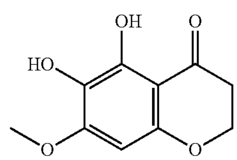 |
| 11a | 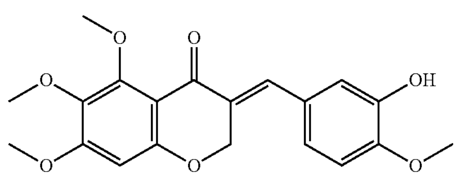 |
| 11b | 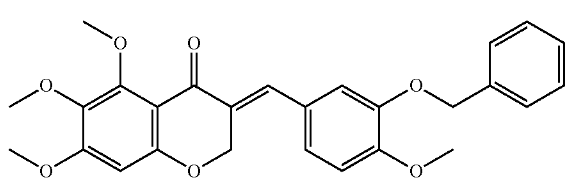 [SMILES: COc1ccc(/C=C2\COc3cc(OC)c(OC)c(OC)c3C2=O)cc1OCc1ccccc1] |
| 11c | 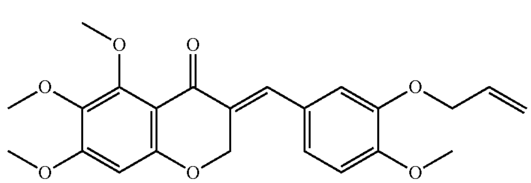 [SMILES: C=CCOc1cc(/C=C2\COc3cc(OC)c(OC)c(OC)c3C2=O)ccc1OC] |

TABLE 1-continued

Synthetic Cremastranone Analogues

| Compound No. | Structure |
|---|---|
| 11d | (structure) |
| 11e | (structure) |
| 11f | (structure) |
| 11g | (structure) |
| 11h | (structure) |
| 11i | (structure) |
| 11j | (structure) |
| 11k | (structure) |

TABLE 1-continued

Synthetic Cremastranone Analogues

| Compound No. | Structure |
|---|---|
| 11l | 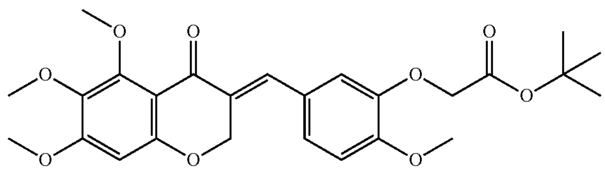 [SMILES: COc1ccc(/C=C2\COc3cc(OC)c(OC)c(OC)c3C2=O)cc1OCC(=O)OC(C)(C)C] |
| 11m | 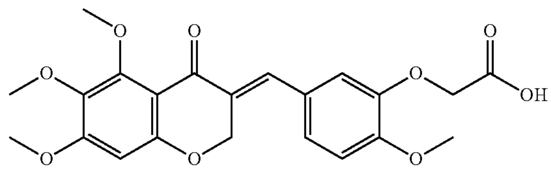 [SMILES: COc1ccc(/C=C2\COc3cc(OC)c(OC)c(OC)c3C2=O)cc1OCC(=O)O] |
| 11n | 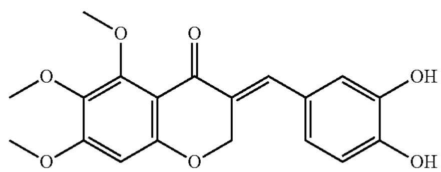 [SMILES: COc1cc2c(c(OC)c1OC)C(=O)/C(=C/c1ccc(O)c(O)c1)CO2] |
| 11o | 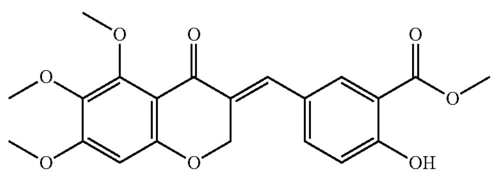 |
| 11p | 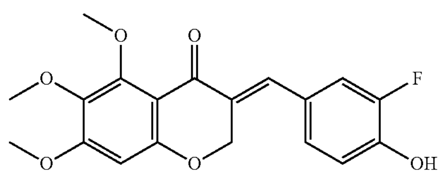 [SMILES: COc1cc2c(c(OC)c1OC)C(=O)/C(=C/c1ccc(O)c(F)c1)CO2] |
| 11q | 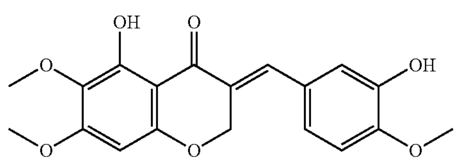 |
| 11r | 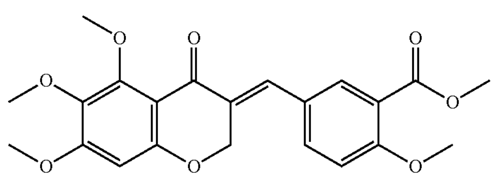 |
| 11s | 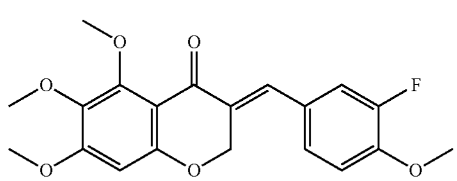 |

TABLE 1-continued

Synthetic Cremastranone Analogues

| Compound No. | Structure |
|---|---|
| 11t | 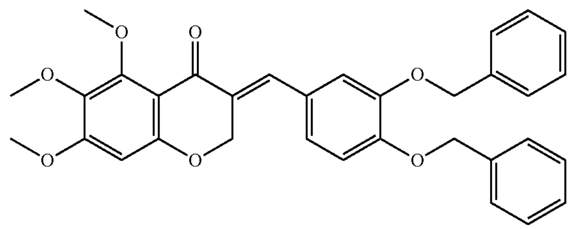 [SMILES: COc1cc2c(c(OC)c1OC)C(=O)/C(=C/c1ccc(OCc3ccccc3)c(OCc3ccccc3)c1)CO2] |
| 11u | 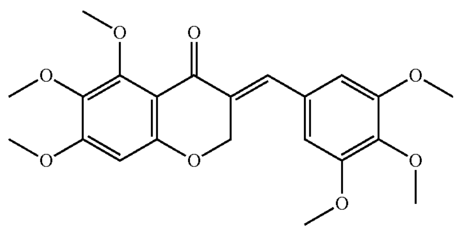 |
| 11v | 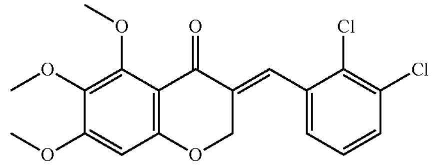 [SMILES: COc1cc2c(c(OC)c1OC)C(=O)/C(=C/c1cccc(Cl)c1Cl)CO2] |
| 11w | 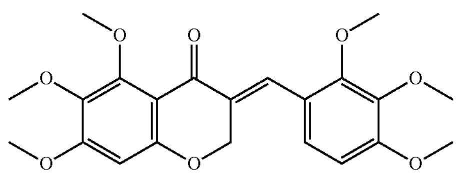 |
| 11x | 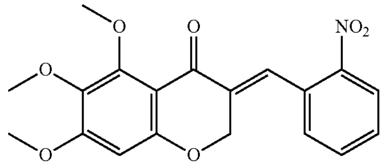 [SMILES: COc1cc2c(c(OC)c1OC)C(=O)/C(=C/c1ccccc1[N+](=O)[O-])CO2] |
| 12 | 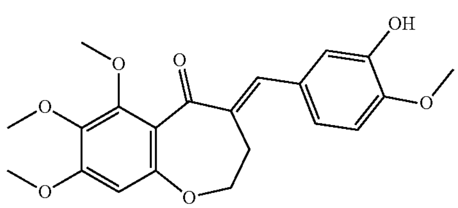 |
| 13 | 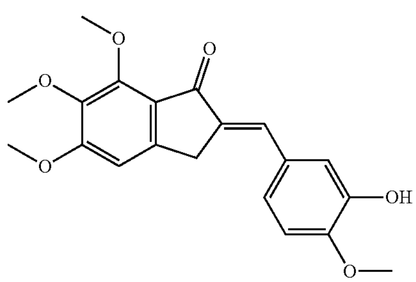 |

TABLE 1-continued

Synthetic Cremastranone Analogues

| Compound No. | Structure |
|---|---|
| 14 | (structure) |
| 15a | (structure) |
| 15b | (structure) |

The composition of the present disclosure further includes one or more additional anti-angiogenic agents in combination with the cremastranone analog, including one or more of: antisense RNA, RNA silencing or RNA interference (RNAi) of angiogenic factors, including ribozymes that target VEGF expression; FOVISTA® and other agents targeting platelet derived growth factor; squalamine; X-82 (Tyrogenix, Needham Heights, Mass.); PAN-90806 (Pan-Optica, Bernardsville, N.J.); TNP470 (Sigma-Aldrich, St. Louis, Mo.) and fumagillin; protein kinase C inhibitors; inhibitors of VEGF receptor kinase such as regorafenib and pazopanib; pigment epithelium derived factor (PEDF); endostatin; angiostatin; anecortave acetate; triamcinolone; verteporfin, photofrin, 5-aminolevulinic acid and other photosensitizers used with photodynamic therapy. As used herein, "anti-angiogenic agent" refers to an agent (e.g., small molecule, protein, siRNA, and the like) capable of inhibiting or reducing angiogenesis in a subject.

In one particular embodiment, the composition of the present disclosure further includes an anti-vascular endothelial growth factor (anti-VEGF) agent in combination with any of the cremastranone analog described above. Exemplary anti-VEGF agents include pegaptanib, ranibizumab, aflibercept, bevacizumab, and combinations thereof.

The compositions of the disclosure may further include one or more pharmaceutically acceptable carriers. As used herein, the phrase "pharmaceutically acceptable" refers to those ligands, materials, formulations, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. The phrase "pharmaceutically acceptable carrier", as used herein, refers to a pharmaceutically acceptable material, formulation or vehicle, such as a liquid or solid filler, diluent, excipient, solvent or encapsulating material, involved in carrying or transporting the active agent/compound from one organ or portion of the body, to another organ or portion of the body. Each carrier must be "acceptable" in the sense of being compatible with the other components of the composition (e.g., synthetic compound) and not injurious to the subject. Lyophilized compositions, which may be reconstituted prior to administration, are also within the scope of the present disclosure.

Pharmaceutically acceptable carriers may be, for example, excipients, vehicles, diluents, and combinations thereof. For example, where the compositions are to be administered orally, they may be formulated as tablets, capsules, granules, powders, or syrups; or for parenteral administration, they may be formulated as injections (intramuscular, subcutaneous, intramedullary, intrathecal, intraventricular, intravenous, intravitreal, subretinal, subconjunctival), drop infusion preparations, or suppositories. For application by the ophthalmic mucous membrane route, they may be formulated as eye drops or eye ointments. These compositions can be prepared by conventional means, and, if desired, the active compound (i.e., synthetic compound) may be mixed with any conventional additive, such as an excipient, a binder, a disintegrating agent, a lubricant, a corrigent, a solubilizing agent, a suspension aid, an emulsifying agent, a coating agent, or combinations thereof.

It should be understood that the compositions of the present disclosure can further include additional known therapeutic agents, drugs, modifications of the synthetic cremastranone analogs into prodrugs, and the like for alleviating, mediating, preventing, and treating the diseases, disorders, and conditions described herein.

In yet another aspect, the present disclosure is directed to a method of treating neovascular eye disease in a subject in need thereof. The method comprises administering an effective amount of the composition including any of the synthetic cremastranone analogs and anti-VEGF combinations described above. Exemplary neovascular eye disease capable of being treated include retinopathy of prematurity (ROP), "wet" age related macular degeneration (AMD), proliferative diabetic retinopathy (DR), pathological myopia, hypertensive retinopathy, occlusive vasculitis, polypoidal choroidal vasculopathy, uveitic macular edema, central retinal vein occlusion, branch retinal vein occlusion, corneal neovascularization, retinal neovascularization, ocular histoplasmosis, neovascular glaucoma, and the like.

In yet another aspect, the present disclosure is directed to a method of treating an angiogenesis-mediated disease in a subject in need thereof. The method comprising administering an effective amount of the composition including any of the synthetic cremastranone analogs and anti-VEGF combinations described above. Exemplary angiogenesis-mediated diseases capable of being treated include non-ocular hemorrhage, myocardial infarction, stroke, cancer, atherosclerosis, ischaemic heart disease, coronary heart disease, peripheral arterial disease, wound healing disorders, and the like.

The compositions are administered in an effective amount to provide treatments of the above-described diseases and disorders. The phrase "effective amount" of the composition of the disclosure means a sufficient amount of the composition to treat disorders or reduce the symptoms of the disorders, at a reasonable benefit/risk ratio applicable to any medical treatment. It can be understood, however, that the total daily usage of the composition of the disclosure can be decided by the attending physician within the scope of sound medical judgment. The specific effective dose level for any particular patient can depend upon a variety of factors including the disorder being treated and the severity of the disorder; activity of the specific composition employed; the specific pharmaceutical composition employed; the age, body weight, general health, sex and diet of the patient; the time of administration, route of administration, and rate of excretion of the specific composition employed; the duration of the treatment; drugs used in combination or coincidental with the specific combination of cremastranone analog and anti-angiogenic agent employed; and like factors well-known in the medical arts. For example, it is well within the skill of the art to start doses of the composition at levels lower than required to achieve the desired therapeutic effect and to gradually increase the dosage until the desired effect is achieved.

Actual dosage levels of compounds/agents in the pharmaceutical compositions of this disclosure can be varied so as to obtain an amount of the compound/agent(s) that is effective to achieve the desired therapeutic response for a particular patient, compositions and mode of administration. The selected dosage level can depend upon the activity of the particular combination of compounds/agents, the route of administration, the severity of the condition being treated and the condition and prior medical history of the patient being treated. However, it is within the skill of the art to start doses of the compounds/agents at levels lower than required to achieve the desired therapeutic effect and to gradually increase the dosage until the desired effect is achieved.

The pharmaceutical compositions including the combination of compounds/agents and pharmaceutical carriers used in the methods of the present disclosure can be administered to a subset of subjects in need of treatment for neovascular eye disease and treatment for angiogenesis-mediated diseases. Some subjects that are in specific need of treatment for neovascular eye disease and/or treatment for angiogenesis-mediated diseases may include subjects who are susceptible to, or at elevated risk of, experiencing neovascular eye disease (e.g., retinopathy of prematurity, diabetic retinopathy, "wet" age-related macular degeneration, etc.), angiogenesis-mediated diseases, and the like. Subjects may be susceptible to, or at elevated risk of, experiencing neovascular eye disease and/or angiogenesis-mediated diseases due to family history, age, environment, and/or lifestyle. Based on the foregoing, because some of the method embodiments of the present disclosure are directed to specific subsets or subclasses of identified subjects (that is, the subset or subclass of subjects "in need" of assistance in addressing one or more specific conditions noted herein), not all subjects will fall within the subset or subclass of subjects as described herein for certain diseases, disorders or conditions.

The disclosure will be more fully understood upon consideration of the following non-limiting Examples.

EXAMPLES

Example 1

In this Example, the therapeutic potential of SH-11037 in models of ocular neovascularization was analyzed. Further, the synergy of a composition including SH-11037 and anti-VEGF treatments in vitro and in vivo were analyzed.
Methods
In Vitro Proliferation Assay and Synergy Analysis The proliferation of human retinal endothelial cells (HRECs) was monitored by an alamarBlue fluorescence assay as described in Lee et al., Org Biomol Chem, 2014, 12(39): 7673-7. Briefly, 2500 cells in 100 µL Endothelial Basal Medium (EBM) (Lonza) in the presence of 50 ng/mL recombinant human VEGF-165 (Biolegend, San Diego, Calif.), were incubated in 96-well clear bottom black plates for 24 hours followed by 48 hours incubation with either 0.5 µM SH-11037, different concentrations of aflibercept (50, 200, 400, 800 µg/ml), or combination treatment. At the end of the incubation, 11.1 µL of alamarBlue reagent was added and 4 hours after, fluorescent readings were taken on a Synergy H1 plate reader (Biotek) with excitation and emission wavelengths of 560 nm and 590 nm respectively. Data were analyzed using GraphPad Prism software (v. 6.0).

Synergy analysis was performed as previously described by Borisy et al, PNAS, 2002, 100(13): 7977-82. The excess inhibition over the highest single agent (HSA) represents the inhibition of the combination mixture over the highest effect seen with either single agent alone at the same concentration as in the mixture. Bliss additivity calculates the predicted combined response C for two single compounds/agents with effects A and B as: C=A+B−A*B. The predicted effect C was then subtracted from the experimentally observed percent inhibition to generate excess over Bliss values, where positive values indicate synergistic effects.

Mice

All mouse experiments followed the guidelines of the Association for Research in Vision and Ophthalmology Statement for the Use of Animals in Ophthalmic and Visual Research and were approved by the Indiana University School of Medicine Institutional Animal Care and Use Committee. Wild-type female C57BL/6J mice, 6-8 weeks of age, were purchased from the Jackson Laboratory (Bar Harbor, Me.). Intraperitoneal injections of 17.5 mg/kg ketamine hydrochloride and 2.5 mg/kg xylazine mixture were used for anesthesia.

Intravitreal Injections

Injections were given under anesthesia in a 0.5 µL volume using a 33-gauge needle. The needle was kept in place for 1 minute to prevent the reflux of solution when the needle was removed. SH-11037 was dissolved in DMSO then diluted in PBS to a final concentration of 0.5% DMSO. Eyes were numbed with tetracaine solution before the injection, and triple antibiotic ointment was used immediately after the injection to prevent infection. A masked researcher undertook imaging and analysis to avoid bias.

Choroidal Sprouting Assay

Sprouting of choroidal layers was tested as previously described in Shao et a., PLoS One, 2013 8(7): e69552. Briefly, 6-8 week old C57Bl/6J mice eyes were enucleated immediately after euthanasia. Peripheral parts of the choroid/sclera layer were separated and cut into pieces. Choroid fragments were then placed on growth factor-reduced Matrigel™ (30 μL/well; BD Biosciences, San Jose, Calif.) in 24-well plates. The plates were then incubated at 37° C. for about 10 minutes to allow the Matrigel to solidify. Endothelial Growth Medium (EGM-2) was prepared by mixing the contents of an EGM-2 "Bullet Kit" (Cat no. CC-4176) with Endothelial Basal Medium (EBM) (Lonza, Walkersville, Md.). Penicillin-streptomycin and 2.5 mg/mL Plasmocin were added to the final medium and used for this assay. Medium (500 μL) was added to each well of the plate and incubated at 37° C. with 5% $CO_2$ for 72 hours before any treatments were added. Medium was changed after 48 hours. SH-11037 was synthesized as taught in WO2014/182695 (incorporated by reference to the extent it is consistent herewith) and dissolved in DMSO and then tested at 0.03, 0.3, and 1 μM concentrations for 48 hours. The final concentration of DMSO in each well was 0.2%. Trypan blue 0.4% solution (Fisher Scientific, Pittsburgh, Pa., USA) was used to assess cell viability. Images were taken using an EVOS-fl digital microscope (AMG, Mill Creek, Wash., USA) and data were analyzed as the sprouting distance in four different directions using ImageJ software v. 1.48V.

In Vivo Toxicity

Toxicity of intravitreally injected SH-11037 was initially assessed by histology and immunofluorescence. The presence of acute ocular toxicity was investigated by injecting SH-11037 at different concentrations (0.1, 1, 10, and 100 μM), while long-term effects were tested by injecting 10 μM SH-11037. Mice were sacrificed 3 and 14 days post injections, respectively. Eyes were enucleated and fixed in 4% PFA overnight, and then the eyes were paraffin embedded and sectioned at 5 μm thickness by the Indiana University School of Medicine Histology Core. Mayer's hematoxylin and eosin (H&E) staining was performed, and retinal morphology was quantified by calculating the ratio of A (the distance from the ganglion cell layer to the outer edge of the inner nuclear layer) to B (the distance from the ganglion cell layer to the outer edge of the outer nuclear layer).

For immunofluorescence, sections were deparaffinised with xylenes and ethanol series and boiled in citrate buffer for 5 minutes. Sections were blocked for one hour with 10% DAKO blocking buffer (DAKO, Carpinteria, Calif.) in Tris-buffered saline (TBS), then probed overnight at 4° C. with primary antibodies diluted 1:400 in 10% DAKO diluent in TBS: GFAP (D1F4Q) and cleaved caspase 3 (D175) (Cell Signaling Technologies, Danvers, Mass.) and MCP1 (Novus Biologicals, Littleton, Colo.). Sections were then incubated with Alexa-fluor 555-conjugated goat anti-rabbit antibody (Life Technologies, Waltham, Mass.) for 1 hour, 1:400 in TBS. TUNEL staining was performed using Click-iT TUNEL assay kit (Fisher Scientific, Pittsburgh, Pa., USA) as per the manufacturer's instructions after the citrate-washing step. Sections were washed with TBS, dehydrated through an ethanol series, then mounted with Vectashield mounting medium with DAPI (Vector Labs, Burlingame, Calif.). Images were taken with an LSM700 confocal microscope (Zeiss, Thornwood, N.Y.) with 40× magnification.

Retinal Electrophysiology and Vasculature Staining

Electroretinograms (ERG) were obtained from animals 14 days post intravitreal injection of 100 μM SH-11037, 0.2 ng mouse anti-VEGF neutralizing antibody (R&D Systems, Minneapolis, Minn., USA)+0.3 μM SH-11037, or vehicle control and performed as described in Cai et al., EMBO Mol Med, 2012 4(9):980-91. Briefly, scotopic rod recordings were performed on overnight dark-adapted mice, with 10 increasing light intensities of white light and responses were recorded with a visual electrodiagnostic system (UTAS-E 2000; LKC Technologies, Gaithersburg, Md.). Stimuli were presented at intensities of 0.025, 0.25, and 2.5 log cd·s/$m^2$ at 10-, 20-, and 30-second intervals, respectively. Ten responses were recorded and averaged at each light intensity. Photopic cone recordings were done after mice were light adapted to a white background light of 100 cd·s/$m^2$ for 8 minutes. Recordings were performed with four increasing flash intensities from 0, 5, 10 and 25 log cd·s/$m^2$ in the presence of a constant 100 mcd·s/$m^2$ rod suppressing background light. The b-wave amplitude was determined from a-wave trough to b-wave peak, behind the last prominent oscillatory potential. Preparation of retina flatmount and staining of pre-existing vasculature was performed as described in Basavarajappa et al., J Med Chem, 2015 58(12):5015-27.

Laser-Induced Choroidal Neovascularization

Laser photocoagulation was performed as described in Sulaiman et al., J Ocul Pharmacol Ther, 2015 and Poor et al., Invest Opthalmol Vis Sci, 2014 55(10): 6525-34. Briefly, eyes were dilated using 1% tropicamide, then underwent laser treatment using 50 μm spot size, 50 ms duration, and 250 mW pulses of an ophthalmic argon green laser, wavelength 532 nm, coupled to a slit lamp. A coverslip was used to allow viewing of the posterior pole of the eye. Each eye received 3 laser burns centered around the optic nerve at 12, 3, and 9 o'clock positions. The appearance of a bubble at the site of laser application was used to identify laser-induced damage of Bruch's membrane. Lesions in which bubbles were not observed were excluded from analysis. The effect of SH-11037 on the L-CNV model using final estimated vitreal concentrations of 0.1, 0.3, 1, or 10 μM SH-11037 was tested. Anti-mouse VEGF164 neutralizing antibody (R&D Systems, Minneapolis, Minn.) was tested at 0.2, 1, and 5 ng/eye. Vehicle (PBS+0.5% DMSO) was used as a negative control. All injections were given a single time, immediately after laser treatment. In testing the effects of SH-11037 on existing L-CNV lesions, vehicle, anti-VEGF164, and SH-11037 (10 μM) injections were given a single time, 5 days post laser.

Optical Coherence Tomography and Fluorescein Angiography

Optical coherence tomography (OCT) was performed at the indicated times using the Micron III intraocular imaging system (Phoenix Research Labs, Pleasanton, Calif.). Before the procedure, eyes were dilated with 1% tropicamide solution (Alcon, Fort Worth, Tex.) and lubricated with hypromellose ophthalmic demulcent solution (Gonak) (Akorn, Lake Forest, Ill.). Mice were then placed on a custom heated stage that moves freely to position the mouse eye for imaging. Several horizontal and vertical images were taken per lesion to allow calculation of CNV lesion volume. Three-dimensional quantification of CNV lesion volumes was performed using an ellipsoid quantification method as described in Sulaiman et al., J Ocul Pharmacol Ther, 2015, 31(8):447-54. FA was performed 14 days post laser by intraperitoneal injections of 50 μL of 25% fluorescein sodium (Fisher Scientific, Pittsburgh, Pa.). Fundus images were taken using the Micron III system and Streampix software.

Choroidal Flatmount and Analysis

Choroidal flatmount preparation, staining, and imaging were done as described in Sulaiman et al., J Ocul Pharmacol Ther, 2015, 31(8):447-54. ImageJ software was used to analyze Z-stack images; the summation of the whole stained area in each section, multiplied by the distance between sections (3 µm) was used as an index for the CNV lesion volume. The volumes of the 3 lesions in each eye were averaged and considered as an n=1 for statistical analysis.

Statistical Analyses

Statistical analyses were performed with GraphPad Prism 6 software. Student's t-tests were used to compare retinal thickness measurements, and ERG parameters. Two-way ANOVA with Dunnett's post hoc test was used for choroidal sprouting distance measurements. For all other experiments, one-way ANOVA was used to compare between treatments with Tukey's post hoc tests. P values<0.05 were considered statistically significant.

Results

Figure 2A:
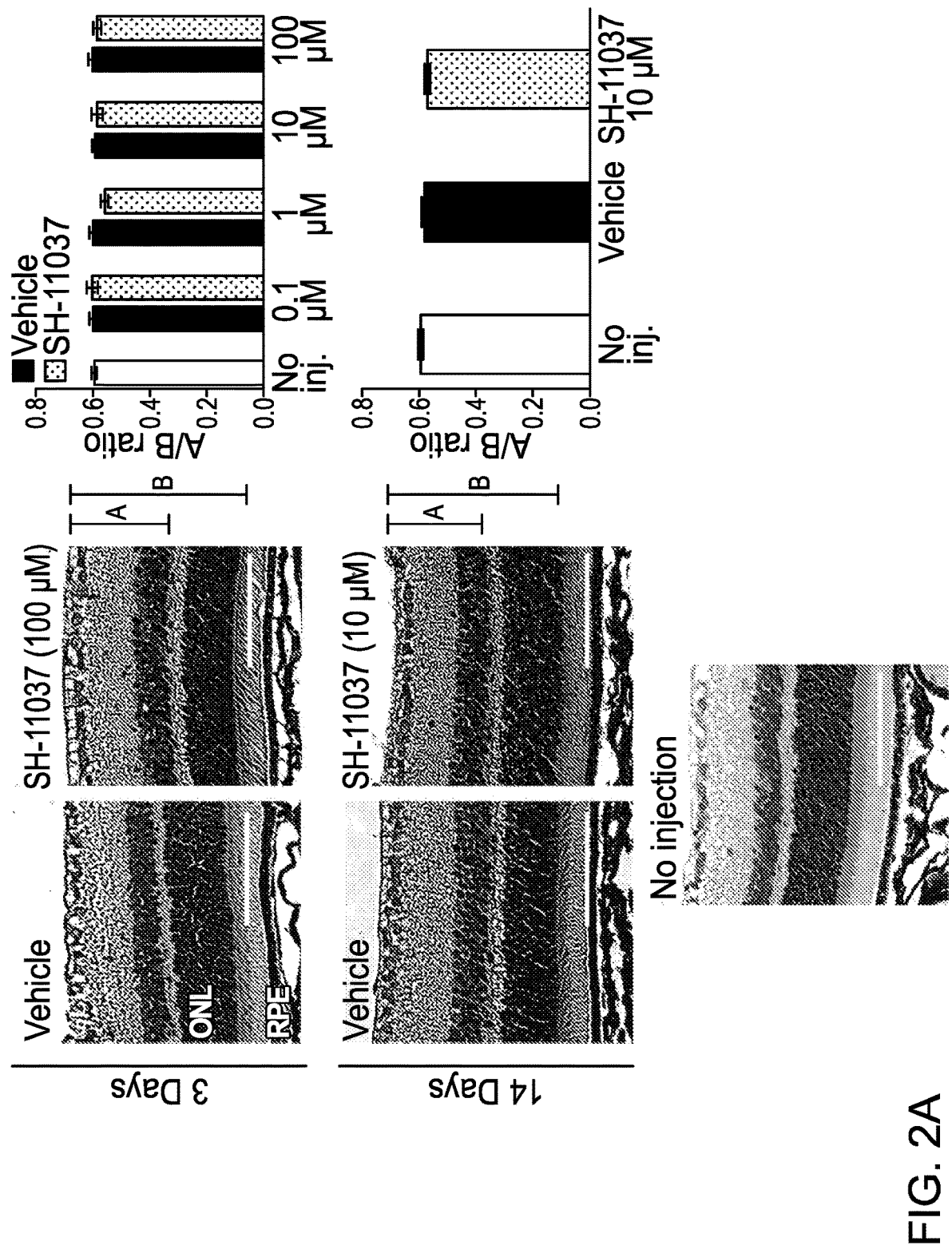
FIGS. 2A-2B depict toxicity effects of intravitreal injection of SH-11037 after 3 and 14 days.
Figure 2B:
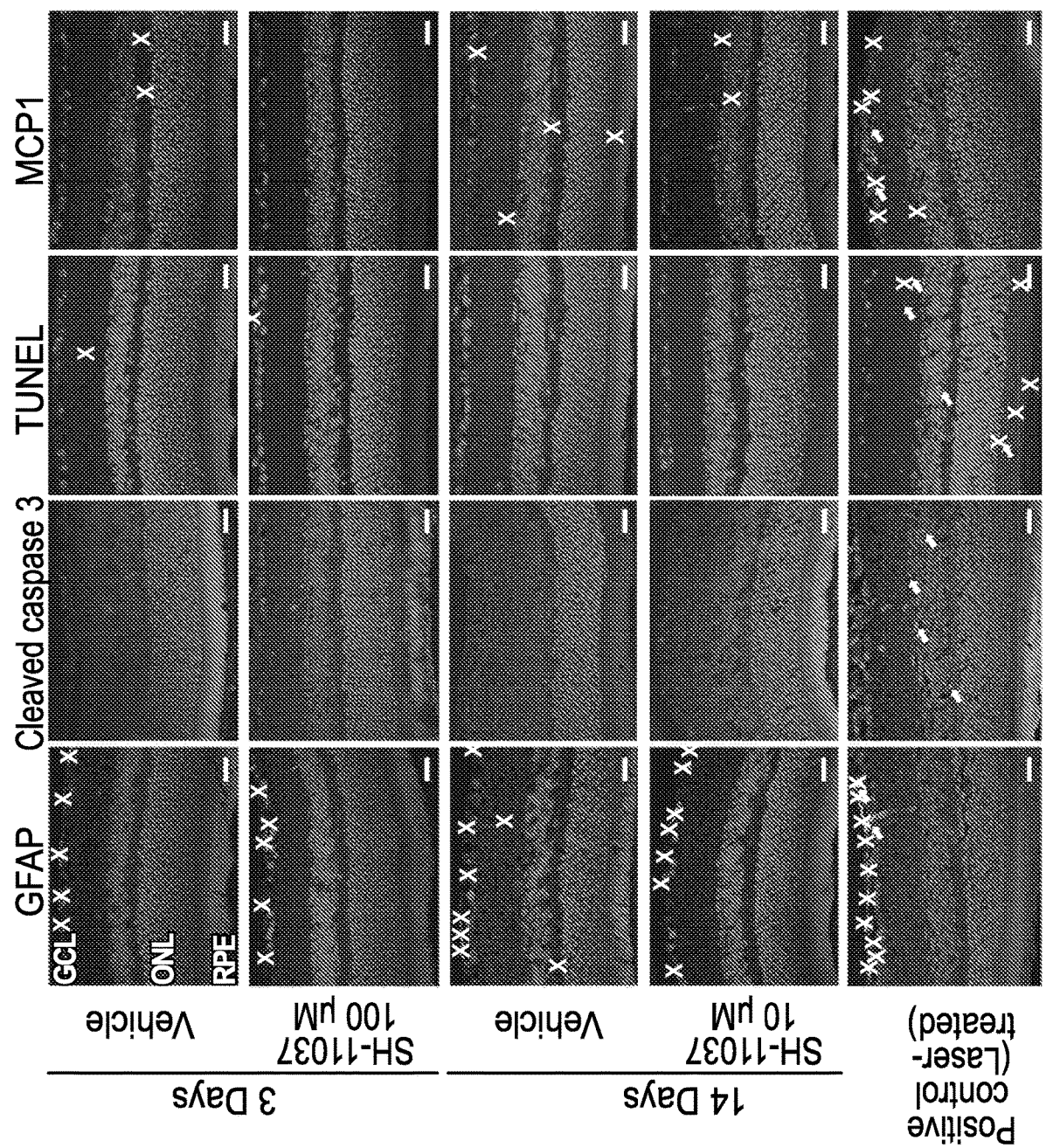

Intravitreal Injection of SH-11037 does not Cause Acute or Chronic Ocular Toxic Effects Before evaluating the therapeutic potential of SH-11037 injections in mammalian eyes, possible toxicity was examined. Signs of acute (3 days post injection) and chronic (14 days post injection) retinal toxicity of intravitreally injected SH-11037 up to 100 µM final concentration in the eye was analyzed. Haematoxylin and eosin (H&E) stained retinal sections of SH-11037 treated eyes revealed no histological changes compared to vehicle treatment and no injection control eyes (FIG. 2A). Quantification of retinal thickness demonstrated the absence of morphological changes between SH-11037 treatments compared to vehicle-treated and uninjected eyes at 3 and 14 days post injections. To further investigate any toxic effects of SH-11037 beyond morphology, retinal sections were stained for glial fibrillary acidic protein (GFAP), cell death markers (cleaved caspase 3, TUNEL) and monocyte chemotactic protein-1 (MCP1) to examine any signs of retinal injury, apoptosis or inflammation, respectively. Neither shorter-nor longer-term SH-11037 treated retina showed any significant increases of GFAP, cleaved caspase 3, TUNEL staining and MCP1 compared to vehicle-treated controls (FIG. 2B). These data suggest the absence of toxic effects of SH-11037 on retina examined 3 and 14 days post injections.

SH-11037 Significantly Suppresses CNV Lesion Volume

Figure 3A:
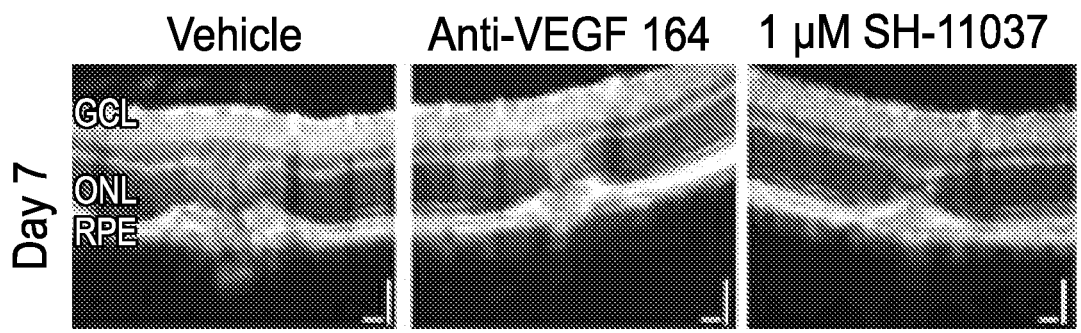
Figure 3B:
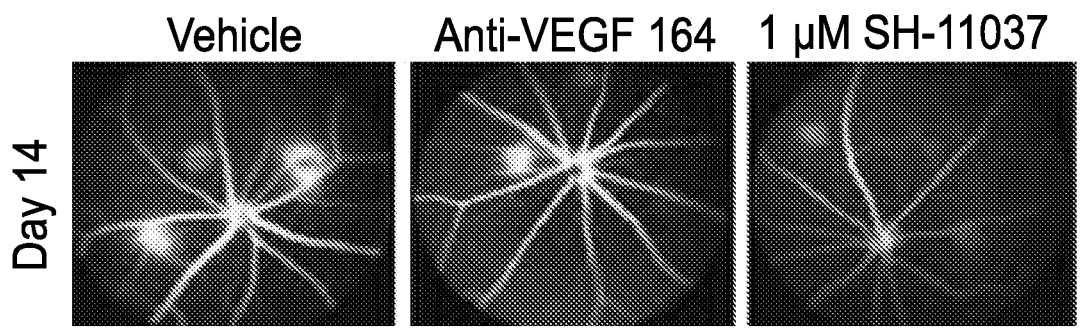
Figure 3C:
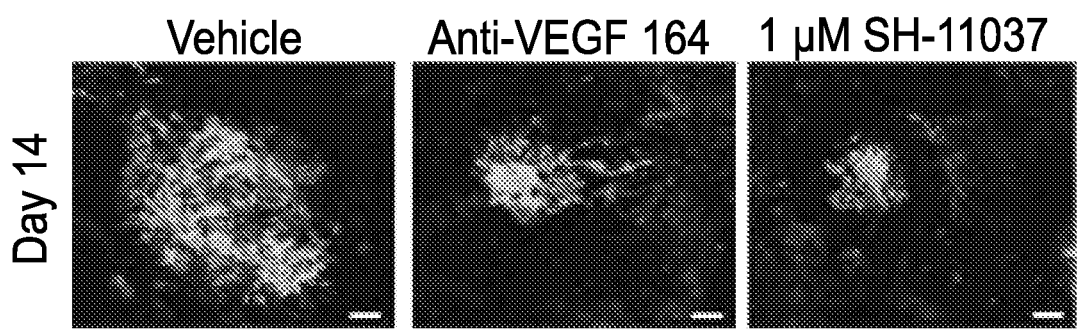

After confirming that SH-11037 was non-toxic, to examine the ability of this compound to reduce choroidal neovascularization in vivo, the standard mouse L-CNV model as described in Lambert et al., Nat Protoc, 2013 8(11):2197-211 was used. Intravitreal injections of different SH-11037 concentrations (0.1, 0.3, 1, 10 µM) were given to C57Bl/6J mice immediately after laser application (FIGS. 3A-3D). The CNV lesion volumes in the SH-11037 treated eyes were significantly lower than those in vehicle treated eyes in a dose-dependent manner at 7 days post-laser, and comparable to those treated with anti-VEGF164 antibody as monitored in vivo by OCT and measured by ellipsoid volume quantification (FIGS. 3A & 3D). Additionally, fluorescein angiography revealed reduced leakiness of CNV lesions from SH-11037 and anti-VEGF164 treated eyes relative to the vehicle treatment (FIG. 3B). Confocal images of agglutinin-stained choroidal flatmounts revealed a reduction in CNV lesion size at 1 and 10 µM SH-11037 and anti-VEGF164 treated eyes compared to vehicle controls (FIG. 3C). Although there was no reduction in the CNV lesion volume compared to the vehicle control in eyes treated with SH-11037 from 0.1 and 0.3 µM, there was a dose-dependent reduction of CNV lesion volume of about 42% at 1 µM and 55% at 10 µM SH-11037 compared to the control eyes (P<0.01) (FIG. 3E). Interestingly, these antiangiogenic effects were comparable to the mouse anti-VEGF164 antibody treatment that demonstrated about 50% inhibition of CNV lesion volume.

SH-11037 Cooperates with Anti-VEGF Therapy In Vitro and In Vivo

Figure 4C:
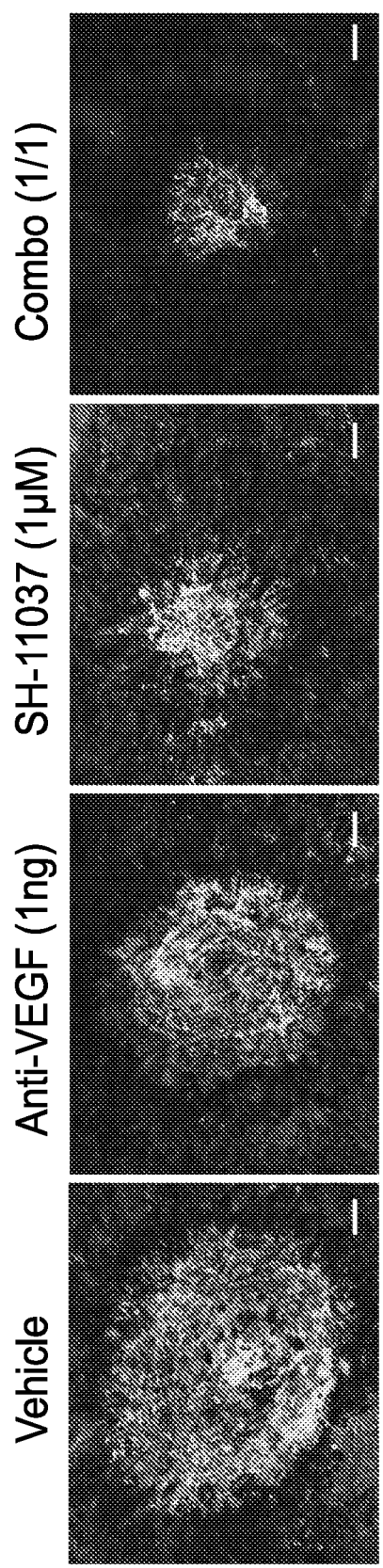

Since most of the complications of anti-VEGF injections are concentration or dosing frequency dependent, the possibility of reducing anti-VEGF dosage by combining with other small molecules is highly desirable. Whether SH-11037 and aflibercept (Eylea; known as VEGF Trap, Regeneron) would have a combined effect on the proliferation of HRECs was first tested using alamarBlue fluorescence assay. Different concentrations of aflibercept (50, 200, 400, and 800 µg/ml) were tested alone and in combination with 0.5 µM SH-11037. Surprisingly, HREC proliferation was significantly inhibited in the presence of combined treatments more than each treatment alone (FIG. 4A). To investigate the nature of the combined effect produced, excess over HSA and excess over Bliss additivity were calculated (FIG. 4B). Values greater than zero observed in both analyses indicate synergistic effects of the tested aflibercept concentrations with 0.5 µM SH-11037.

Figure 4D:
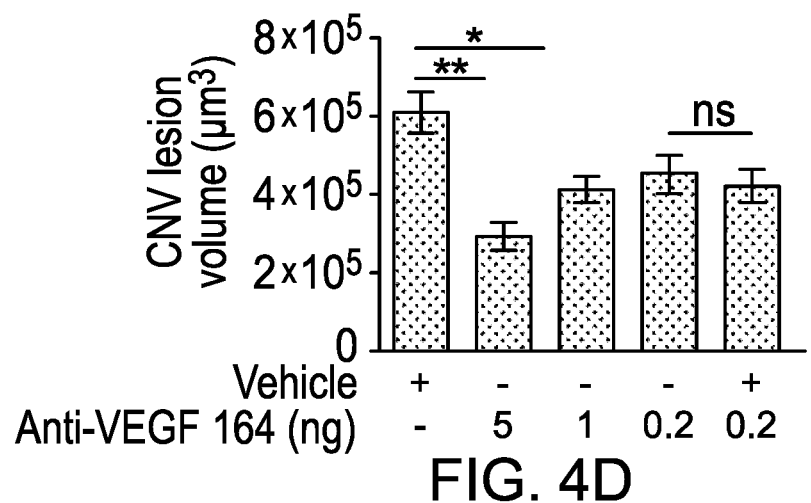
Figure 4E:
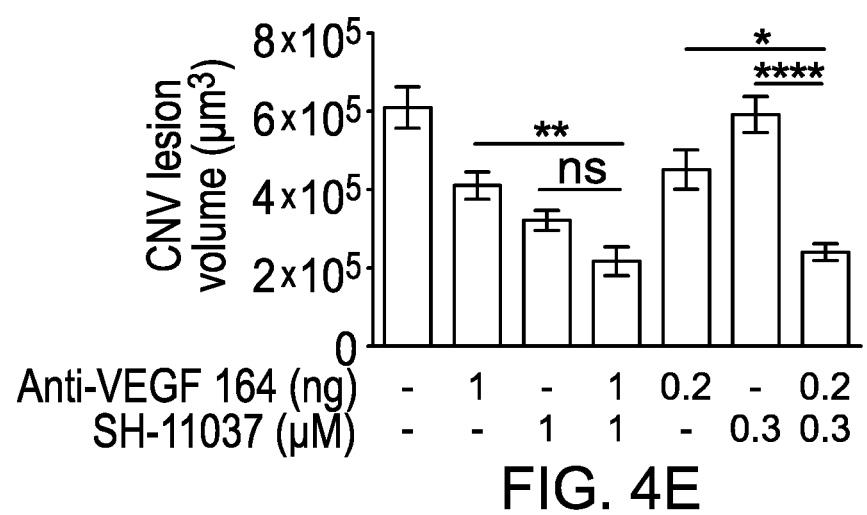
Figure 4F:
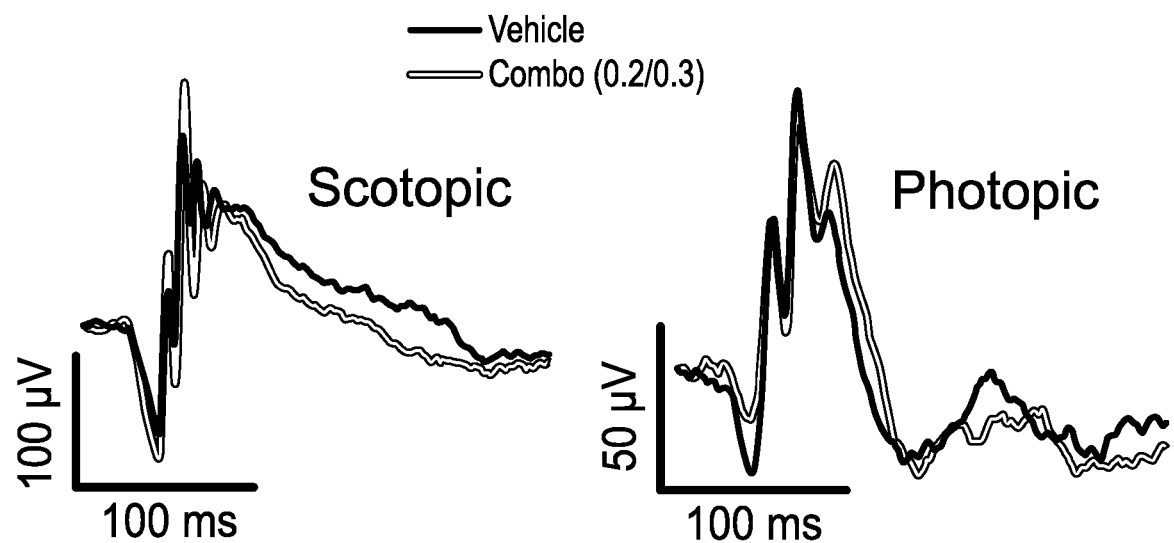
Figure 4G:
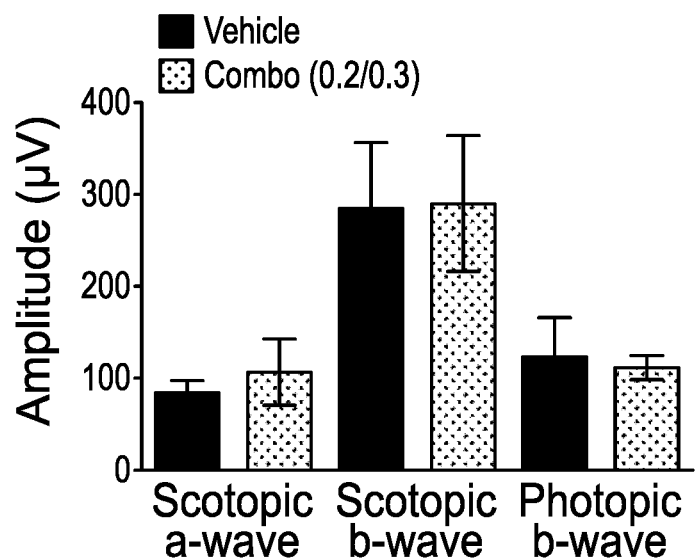

Next, the potential of SH-11037 and anti-VEGF antibody combination in vivo was tested in the LCNV mouse model. The anti-VEGF164 antibody is a murine equivalent of the anti-VEGF antibody-based treatments used in humans, bevacizumab (Avastin, Roche) and ranibizumab (Lucentis, Roche). A dose-response effect of intravitreal injections of SH-11037 and mouse anti-VEGF164 antibody was first established separately (FIGS. 3E, 4D). Based on these results, a combination of the lowest fully active dose of SH-11037, 1 µM, and the suboptimal dose of anti-VEGF164, 1 ng/eye (FIG. 4C) was chosen. Analysis of confocal Z-stack images of agglutinin stained choroidal flatmounts revealed a significant reduction in neovascularization with the combination therapy compared to anti-VEGF164 alone, P<0.001 (FIG. 4E). Moreover, a combination of individually inactive doses of SH-11037 (0.3 µM) and anti-VEGF164 (0.2 ng/ml) caused a significant suppression of CNV lesion volume compared to SH-11037 and anti-VEGF164 alone, P<0.001, and P<0.05, respectively (FIG. 4E), without interfering with retinal function as examined by ERG (FIGS. 4F & 4G). Interestingly, this combination was synergistic, with percent inhibition of 37 and 36 in excess over HSA and Bliss additivity, respectively.

SH-11037 does not Affect Retinal Function and Pre-Existing Vessels

Figure 5A:
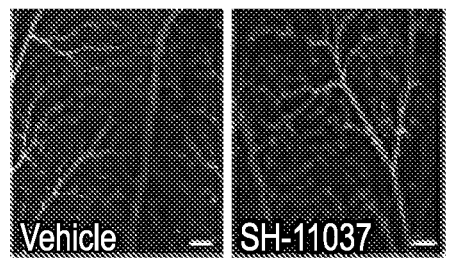
FIGS. 5A-5D depict the effects of SH-11037 on retinal function and pre-existing vasculature.
Figure 5B:
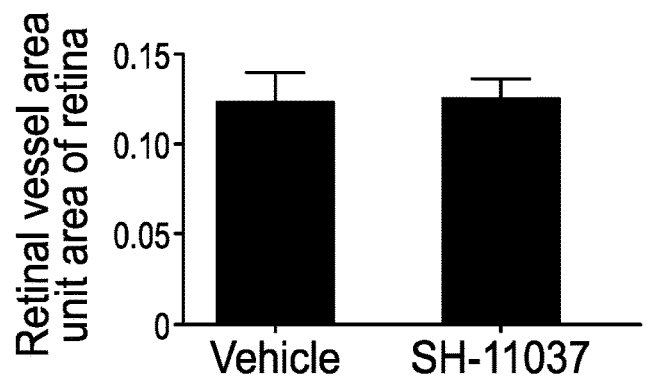
Figure 5C:
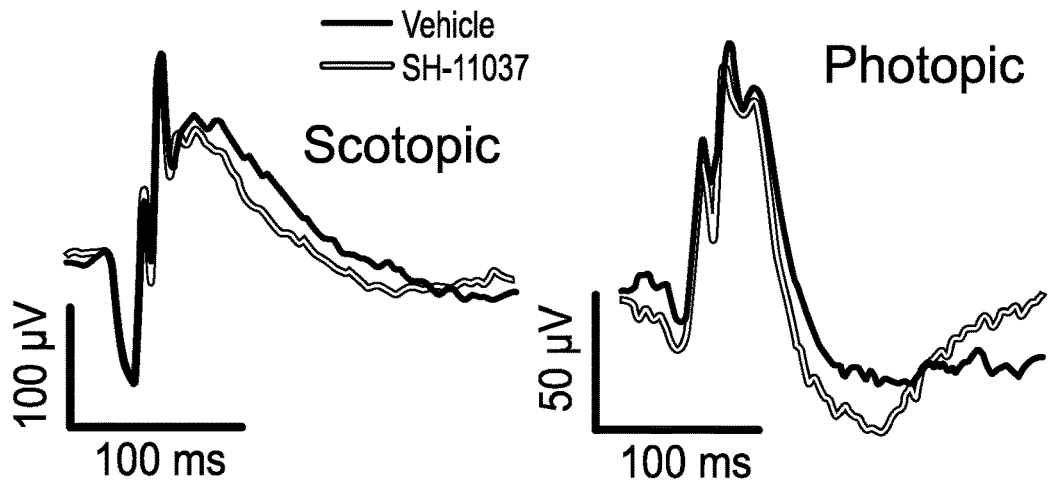
Figure 5D:
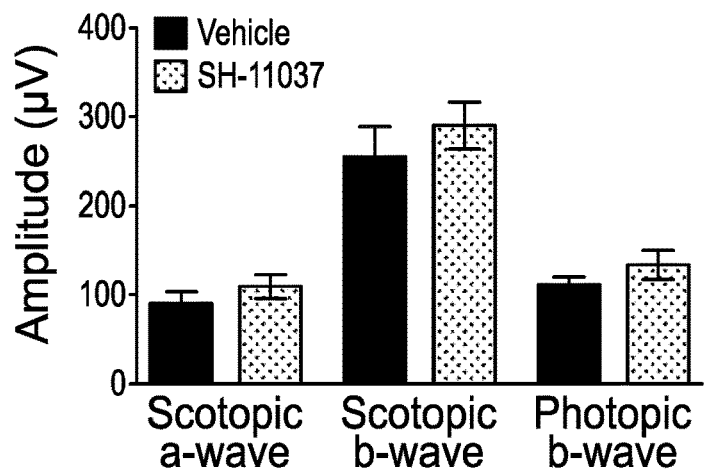

Whether SH-11037 would cause regression of pre-existing retinal vasculature was next examined Whole retina flatmounts were prepared 14 days after 100 µM SH-11037 or vehicle intravitreal injections and stained with isolectin B4 (FIG. 5A). No changes in the pre-existing retinal vessels were observed after SH-11037 treatment compared to the vehicle control. Moreover, ERG was used to evaluate changes in the function of neural retina 14 days after 100 µM SH-11037 injections. Scotopic a- and b-waves, and photopic b-waves were not significantly different in SH-11037 treated eyes relative to the control eyes (FIGS. 5B & 5C). These results demonstrate that SH-11037 does not interfere with the function of neural retina or the maintenance of normal retinal vasculature.

SH-11037 Inhibits Choroidal Neovascularization Ex Vivo in the Choroidal Sprouting Assay.

Figure 6A:
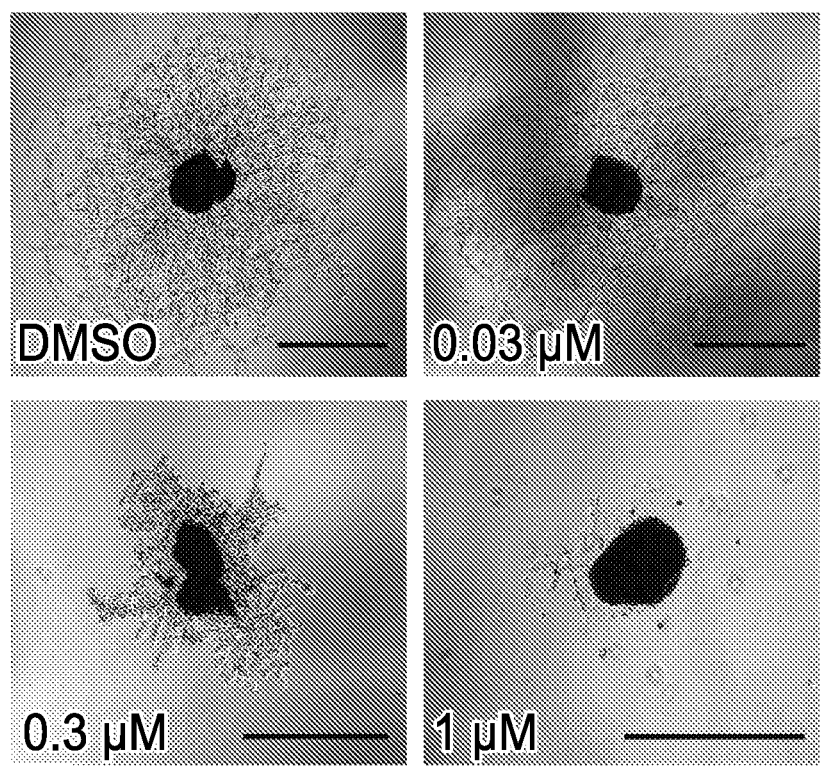
FIGS. 6A-6C depict the effect of SH-11037 on choroidal sprouting without affecting cell viability.
Figure 6B:
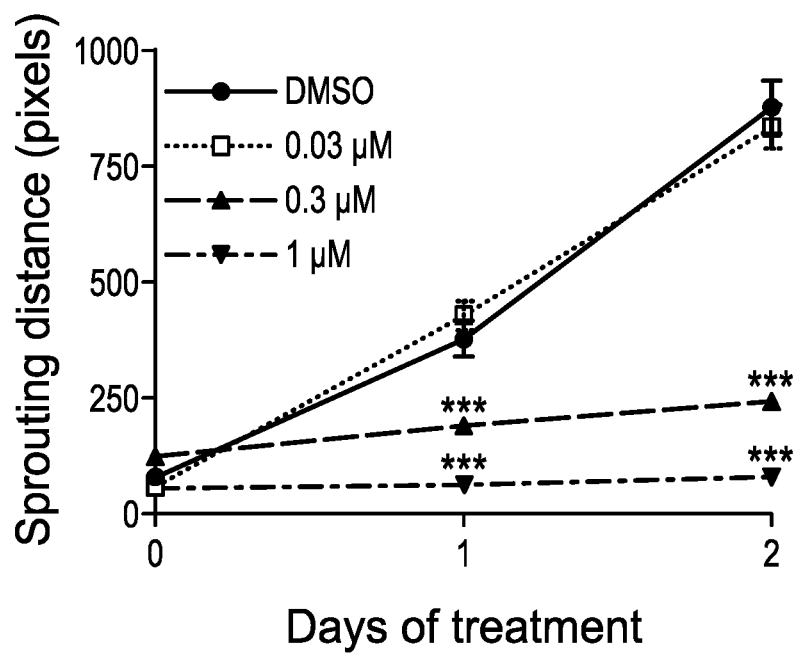
Figure 6C:
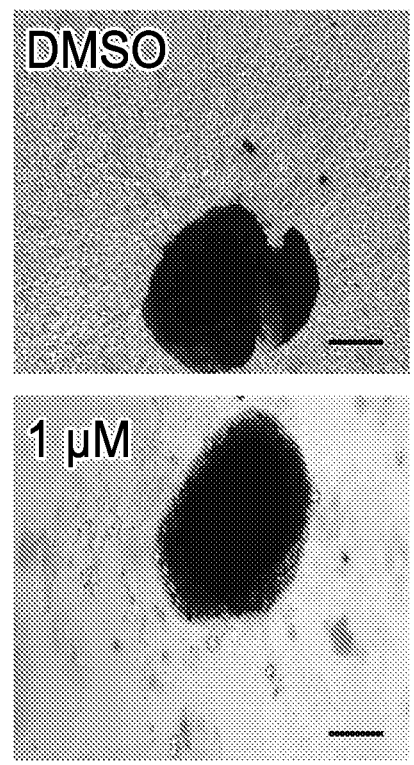

To further investigate the effect of SH-11037 on choroidal angiogenesis, different concentrations of SH-11037 were tested on the sprouting of mouse choroidal tissues ex vivo. After 48 hours of incubation with SH-11037, the ability of the choroidal tissues to form sprouts was significantly inhibited in a concentration-dependent manner compared to the vehicle treated controls (FIGS. 6A & 6B). This effect was not due to cell death as examined by Trypan blue staining for viable cells that indicated the absence of significant cell death in SH-11037 treated wells compared to DMSO controls (FIG. 6C).

SH-11037 Suppressed Pre-Existing CNV Lesions

Figure 7A:
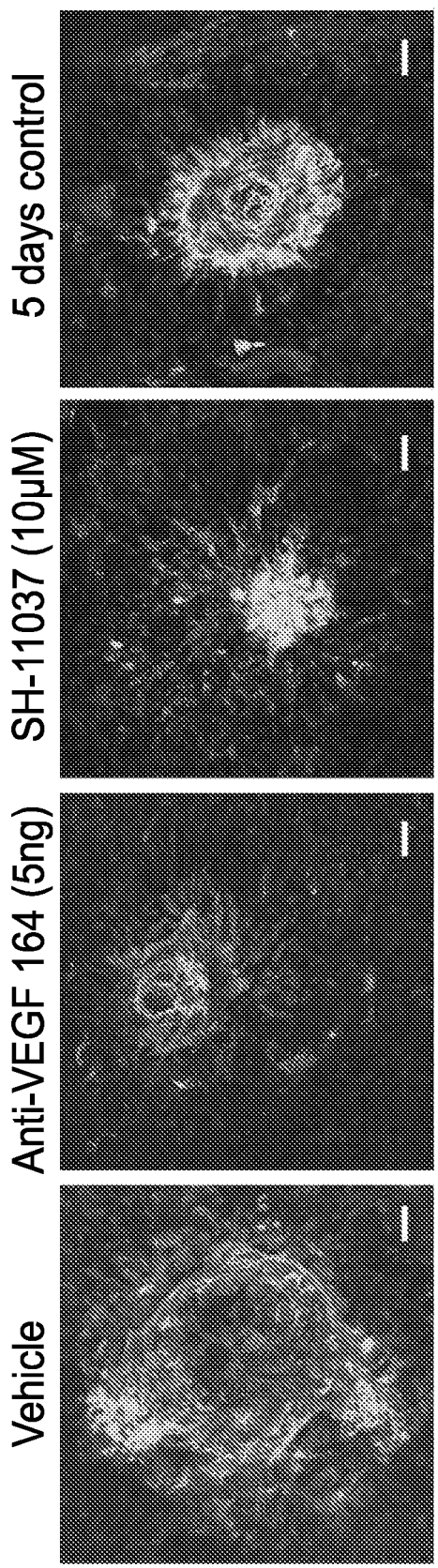
FIGS. 7A & 7B depict the effect of treatment with SH-11037 on already-established CNV lesion volume, rather than prevention of CNV formation alone.
Figure 7B:
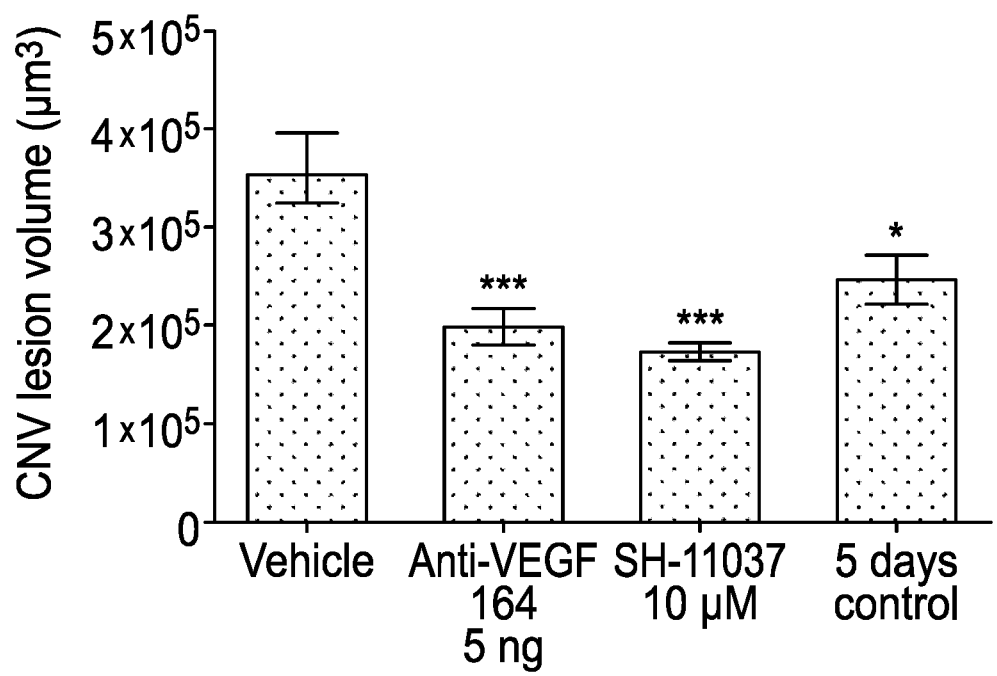

In order to assess the therapeutic potential of SH-11037 injections in a more clinically relevant environment, the effect of SH-11037 on pre-existing CNV lesions was tested. In this experiment, intravitreal injections were given a single time, 5 days post laser, and CNV lesion volumes were quantified 14 days post laser. Interestingly, SH-11037 significantly suppressed CNV lesion vascular volumes relative to the vehicle treatment. This effect was comparable to the standard anti-VEGF164 antibody indicating a strong therapeutic potential of SH-11037 (FIGS. 7A & 7B). In order to understand whether SH-11037 only prevents further development of CNV lesions or resolves pre-existing ones, CNV vascular volumes were evaluated 5 days post-laser before the administration of any treatments. Interestingly, 5 days control eyes were significantly lower than the vehicle treatment at 14 days. However, there was no significant difference between the 5 days control and SH-11037 and anti-VEGF164 treatments, suggesting that both treatments worked mainly by blocking further growth of CNV lesions.

Discussion

In the present Example, the pharmacological activity and safety of SH-11037 in the context of ocular angiogenesis was analyzed. Endothelial cells from different vascular beds have different physiological properties. Therefore, the effects of SH-11037 in microvascular tissues of the choroid ex vivo were evaluated, taking advantage of the capability of the choroidal sprouting assay to measure microvascular angiogenesis in the choroid. SH-11037 demonstrated a potent inhibitory concentration, 0.03 µM, which was consistent with the growth inhibitory concentration observed in vitro in retinal microvascular endothelial cells.

Up to 100 µM SH-11037 was not associated with short or long-term signs of ocular toxicity in mouse retina, when the compound was injected intravitreally. It did not interfere with retinal function or the existing retinal vasculature, suggesting that SH-11037 specifically targets proliferating endothelial cells.

In a subpopulation of human patients, anti-VEGF inhibitors can cause adverse effects in multiple organs including the eye. Some of these complications, such as retinal detachment and loss of neural retinal cells, are related to the doses of anti-VEGF treatment given to the patient; thus, lowering anti-VEGF doses while maintaining the therapeutic efficacy would be beneficial. It was hypothesized that anti-VEGF therapy treatment could be reduced by combining it with SH-11037. The hypothesis was first tested in vitro using aflibercept, an exemplar anti-angiogenic agent that is a fusion protein that consists of VEGF receptor-binding sequences fused to a segment of a human antibody backbone. Aflibercept is used in the clinic for the treatment of wet AMD and other neovascular eye diseases. Surprisingly, SH-11037 produced combined effects with different concentrations of aflibercept in inhibiting the proliferation of HRECs, which were more pronounced than each treatment alone. Moreover, the in vivo data in the L-CNV model indicate that by combining 1 ng anti-VEGF164 antibody with 1 µM SH-11037, the dose of anti-VEGF164 can be reduced 5-fold while maintaining the same efficacy as a full dose. This is valuable in reducing the adverse effects associated with anti-VEGF therapy.

While the combination's effect was not significantly different from the overall inhibitory effect of SH-11037, this was likely due to the production of the maximal inhibition using 1 µM SH-11037 that obscured any further combined effects with anti-VEGF164. Therefore, a combination of sub-efficacious doses of SH-11037 and anti-VEGF164 were tested. The combination of two individually inactive doses of SH-11037 (0.3 µM), and anti-VEGF164 (0.2 ng) produced a significant inhibition of L-CNV lesions that was comparable to the fully active dose of either treatment alone. SH-11037 and anti-VEGF combinations tested in vitro and in vivo appeared synergistic according to excess over HSA and Bliss additivity, two established methods of assessing synergy.

What is claimed is:

1. A composition comprising 0.5 µM SH-11037 having the formula:

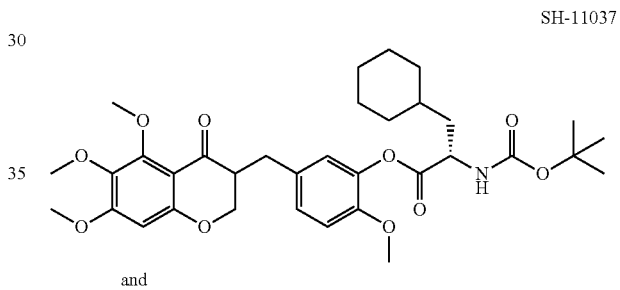

SH-11037 and from 50 µg/ml to 800 µg/ml of aflibercept.

2. The composition as set forth in claim 1 further comprising a pharmaceutically acceptable carrier.

3. A method of treating a neovascular eye disease in a subject in need thereof, the method comprising administering an effective amount of the composition of claim 1 and a pharmaceutically acceptable carrier.

4. The method as set forth in claim 3 wherein the neovascular eye disease is selected from the group consisting of retinopathy of prematurity, diabetic retinopathy, wet age-related macular degeneration, pathological myopia, hypertensive retinopathy, occlusive vasculitis, polypoidal choroidal vasculopathy, uveitic macular edema, central retinal vein occlusion, branch retinal vein occlusion, corneal neovascularization, retinal neovascularization, ocular histoplasmosis, and neovascular glaucoma.

5. The method as set forth in claim 3 wherein the neovascular eye disease is selected from the group consisting of corneal neovascularization and retinal neovascularization.

6. A method of treating an angiogenesis-mediated disease in a subject in need thereof, the method comprising administering an effective amount of the composition of claim 1 and a pharmaceutically acceptable carrier.

7. The method as set forth in claim 6 wherein the angiogenesis-mediated disease is selected from the group consisting of non-ocular hemorrhage, myocardial infarction, stroke, cancer, atherosclerosis, ischaemic heart disease, coronary heart disease, peripheral arterial disease, wound healing disorder and combinations thereof.

* * * * *